(12) United States Patent
Coyle

(10) Patent No.: US 7,513,171 B2
(45) Date of Patent: Apr. 7, 2009

(54) AUTONOMOUS RAPID FACILITY CHEMICAL AGENT MONITOR VIA SMITH-PURCELL TERAHERTZ SPECTROMETRY

(75) Inventor: Peter J. Coyle, Newton, PA (US)

(73) Assignee: Sarnoff Corporation, Princeton, NJ (US)

( * ) Notice: Subject to any disclaimer, the term of this patent is extended or adjusted under 35 U.S.C. 154(b) by 350 days.

(21) Appl. No.: 11/311,091

(22) Filed: Dec. 19, 2005

(65) Prior Publication Data

US 2008/0060455 A1  Mar. 13, 2008

Related U.S. Application Data

(60) Provisional application No. 60/637,077, filed on Dec. 17, 2004.

(51) Int. Cl.
G01N 1/22 (2006.01)
G01N 21/35 (2006.01)
(52) U.S. Cl. ............. 73/863.23; 73/863.21; 73/863.22; 73/863.71
(58) Field of Classification Search ............. 73/863.01, 73/863.21, 863.22, 863.23, 863.71, 863.81, 73/864.71; 250/338.1, 339.06, 339.07, 390.07, 250/390.08; 356/326
See application file for complete search history.

(56) References Cited

U.S. PATENT DOCUMENTS

| | | | | |
|---|---|---|---|---|
| 3,103,807 A * | 9/1963 | Broerman | | 73/23.42 |
| 3,321,977 A * | 5/1967 | Topham | | 73/863.71 |
| 3,983,864 A * | 10/1976 | Sielaff et al. | | 600/364 |
| 4,246,788 A * | 1/1981 | Olin et al. | | 73/863.03 |
| 4,348,888 A * | 9/1982 | Snee | | 73/23.31 |
| 4,361,027 A * | 11/1982 | Schmitt | | 73/23.2 |
| 5,083,019 A * | 1/1992 | Spangler | | 250/286 |
| 5,187,972 A * | 2/1993 | DeFriez | | 73/23.2 |
| 5,585,575 A * | 12/1996 | Corrigan et al. | | 73/863.71 |
| 5,932,795 A * | 8/1999 | Koutrakis et al. | | 73/28.01 |
| 6,042,634 A * | 3/2000 | Van Tassel et al. | | 95/14 |
| 6,085,601 A * | 7/2000 | Linker et al. | | 73/863.12 |
| 6,244,117 B1 * | 6/2001 | Mengel et al. | | 73/863.21 |
| 6,815,670 B2 * | 11/2004 | Jenkins et al. | | 250/286 |
| 6,828,795 B2 * | 12/2004 | Krasnobaev et al. | | 324/464 |
| 7,041,153 B2 * | 5/2006 | Totoki | | 95/3 |
| 7,261,008 B2 * | 8/2007 | Saaski et al. | | 73/863.22 |
| 2002/0121148 A1 * | 9/2002 | Shinozaki et al. | | 73/863.33 |
| 2003/0230152 A1 * | 12/2003 | McGill et al. | | 73/864.34 |
| 2004/0227088 A1 * | 11/2004 | Trotz et al. | | 250/341.1 |
| 2005/0063865 A1 * | 3/2005 | Bonne et al. | | 422/68.1 |

* cited by examiner

Primary Examiner—David A. Rogers
(74) Attorney, Agent, or Firm—Lowenstein Sandler PC

(57) ABSTRACT

A method and system for sampling high vapor pressure substances is provided. In one embodiment, a sample is preconcentrated by compression and condensation, water is removed by a condensing gas dryer, particulates are removed from the sample with an electrostatic precipitator; and the sample is shuttled through a sintered core at high vapor pressure so that molecules are condensed on the surface of the sintered core. In another embodiment, a system for sampling high vapor pressure substances includes a shuttle having a first piston and second piston for shuttling a sample through a sintered core at high vapor pressure and a condensing heat exchanger between the first piston and the second piston, the condensing heat exchanger including the sintered core.

12 Claims, 16 Drawing Sheets

WAVELENGTH

AUTONOMOUS RAPID FACILITY CHEMICAL AGENT MONITOR VIA SMITH-PURCELL TERAHERTZ SPECTROMETRY

CROSS-REFERENCE TO RELATED APPLICATIONS

This application claims the benefit of U.S. provisional patent application No. 60/637,077 filed Dec. 17, 2004, which is herein incorporated by reference.

BACKGROUND OF THE INVENTION

1. Field of the Invention

The present invention relates to chemical agent monitoring and spectrometry. In particular, this invention relates to a method and apparatus for providing an autonomous rapid facility chemical agent monitor via Smith-Purcell Teraherz spectrometry.

2. Description of the Related Art

There is an increasing demand for systems for military, private or individual use that are capable of detecting and analyzing chemical and biological contaminants, such as explosives (e.g., TNT or DNT). One method of detecting such contaminants uses rotational microwave spectroscopy. The rotational and vibrational modes of molecules (e.g., contaminant molecules) have energies that naturally correspond to energies of photons in a spectrum of radiation. A source generates radiation that interacts with contaminant molecules present in a "target" to be analyzed, so that specific frequencies of emitted radiation are absorbed by the molecules. A detector is positioned to identify the frequencies that fail to transmit through the target, and the failure of a particular frequency to transmit can indicate the presence of a specific absorbing contaminant.

The far infrared (or terahertz) spectrum of radiation is particularly well-suited for use in systems such as that described above, because the spectrum corresponds to the vibrational and rotational modes of many chemicals, including explosives, and contains a great deal of signature information. Unfortunately, work in the terahertz spectrum is made extremely difficult and inconvenient by a lack of coherent sources of radiation that can operate continuously and tuned over a wide range of the terahertz wavelength spectrum.

Therefore, there is a need in the art for a terahertz system that can be used to detect the presence of chemical and biological contaminants.

SUMMARY OF THE INVENTION

The present invention describes a method and apparatus for providing an autonomous rapid facility chemical agent monitor via Smith-Purcell Teraherz spectrometry, including a method and system for sampling high vapor pressure substances.

In one embodiment, a sample is pre-concentrated by compression and condensation, water is removed by a condensing gas dryer, particulates are removed from the sample with an electrostatic precipitator; and the sample is shuttled through a sintered core at high vapor pressure so that molecules are condensed on the surface of the sintered core.

In another embodiment, a system for sampling high vapor pressure substances includes a shuttle having a first piston and second piston for shuttling a sample through a sintered core at high vapor pressure and a condensing heat exchanger between the first piston and the second piston, the condensing heat exchanger including the sintered core.

BRIEF DESCRIPTION OF THE DRAWINGS

So that the manner in which the above recited features of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION

The present invention discloses various embodiments of a method and apparatus for autonomous rapid facility chemical agent monitoring (ARFCAM) via Smith-Purcell (SP) Teraherz spectrometry (THz).

Figure 1:
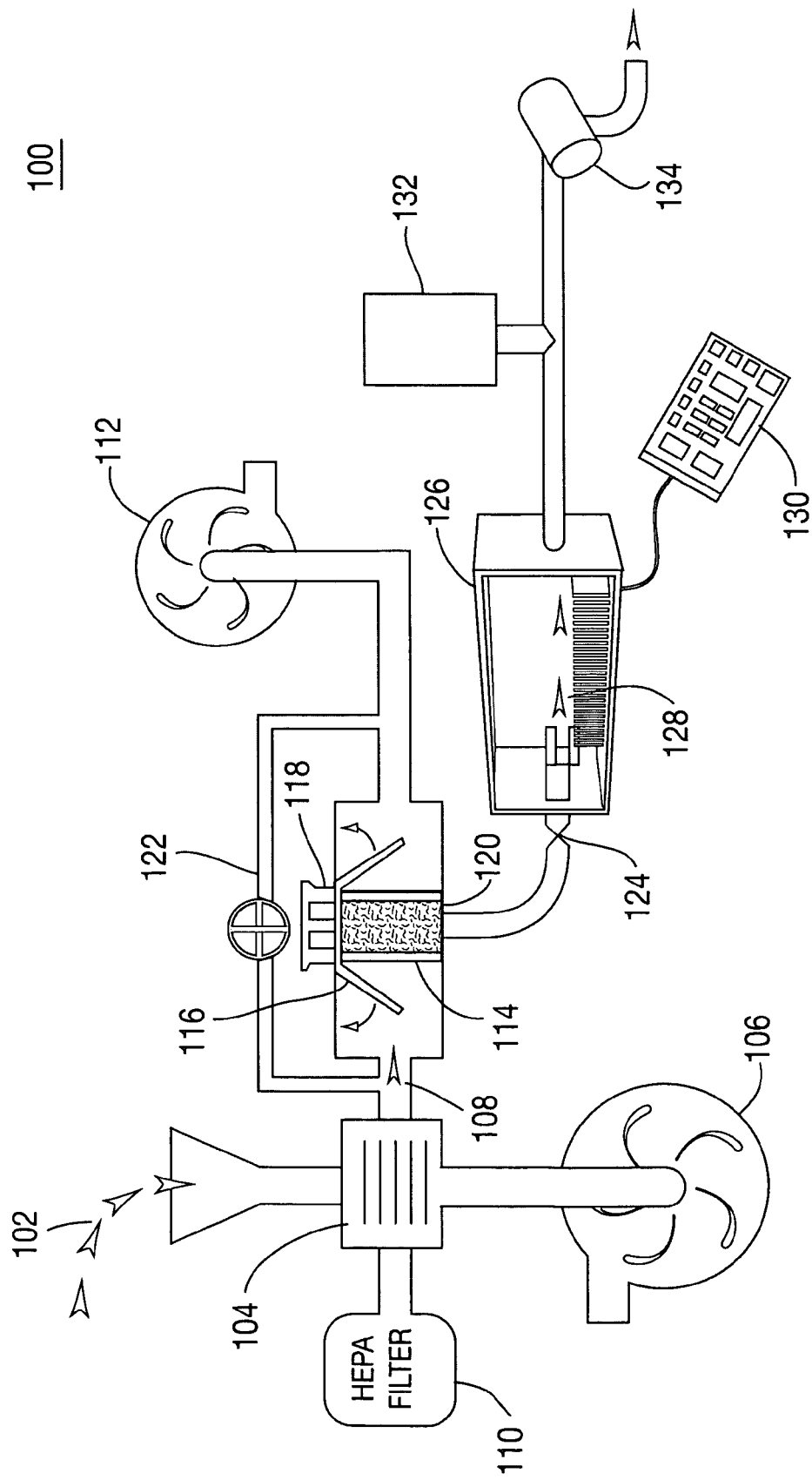
FIG. 1 is a block diagram showing an overview of an exemplary embodiment of the TeraSpec system.

One exemplary embodiment is an autonomous rapid facility chemical agent monitor (ARECAM) system (see, e.g., FIG. 1). This system is a continuous detector to warn facility-monitoring detector that identifies chemical warfare agents (CWA) (e.g., blood, vesicant, nerve, choking, and blister) and toxic industrial chemicals (TIC), among other chemical agents, such as trace explosives. The system is low-cost, highly autonomous, reliable and capable of providing rapid detection and alarm indication of a large range of toxic chemicals despite ambient changes and varying concentrations.

This exemplary embodiment utilizes a unique technical approach that includes SP based THz spectrometry to identify the unique rotational/vibrational spectral signatures of CWAs and TICs. This exemplary embodiment includes methods of analysis and laboratory validation of this approach, including validation of sensitivity, probability of detection, and estimated rates of false positive and negative alarms. The ARFCAM system is an affordable state-of-the-art solution for detecting chemical threats.

One exemplary embodiment is an ARFCAM system called TeraSpec that includes an air collection/concentrator system (ACCS), a SP based intercavity absorption spectrometer (IAS), and a spectral signature analyzer (SSA). The ACCS removes water vapor and particulate matter and provides a concentrated gaseous sample to the IAS. The ACCS also stores collected samples for future forensic analysis. The IAS measures the rotational and vibrational spectra in the THz range. Spectra in the THz range are highly specific to the material and, therefore, give very high selectivity (and, therefore, low false-alarm rates). In one embodiment, the IAS is very sensitive (e.g., demonstrated to about 1 part per trillion). The SSA analyzes the spectra that the IAS produces and, then, triggers an alarm when a TIC or CWA is detected. The SSA not only analyzes the current spectra, but also compares it to an historical spectral record for the site. By comparing current measurements to slowly varying background fluctuations, the SSA maintains a very low false-positive detection rate, while maintaining high detection sensitivity.

TeraSpec Attributes and Performance

One exemplary embodiment is the TeraSpec system that identifies CWAs and TICs using a SP based THz spectrometer. SP based THz spectrometry is highly sensitive and selective when measuring the unique rotational/vibrational spectral signature of individual chemical species. The spectrometer has many benefits, including: high specificity, high sensitivity, rapid detection, broad tunability, and low maintenance. High specificity is achieved, because the unique molecular structure of target chemicals is recognized using the rotational/vibrational molecular Terahertz spectrum. High sensitivity is achieved because the spectrometer is about 100 to 1,000 times more sensitive than traditional, extra-cavity spectrometers and sensitive to chemical agents to about 1 part per trillion. Rapid detection is achieved to nearly instantaneously detect a broad range of chemical agents in approximately <10 seconds. Broad tunability is achieved at about 0.1 THz to 10 THz at 10 KHz resolution. Low maintenance is achieved, because the detector is fully electronic with no consumables, and a mean time between failures (MTBF) of approximately <10,000 hours.

This exemplary embodiment along with compact and efficient collection/concentration techniques and signal processing/noise reduction algorithms, provides a unique, completely autonomous system with a very low false positive (approximately <1/year) and false negative (approximately <5%), making this exemplary embodiment superior to existing solutions. Because the manufacturing cost of the SP THz spectrometer is low, one embodiment includes two spectrometers used in parallel, each tuned to a different spectral band, allowing the exemplary embodiment of the TeraSpec system to cover a very wide spectral range.

Given its high sensitivity, this exemplary embodiment of the TeraSpec system is capable of sensing AEL concentrations within the immediate danger to health and life (IDHL) time limits. For example, a concentration level of eight parts per trillion for GD, (which is a CWA with the lowest air exposure level (AEL) for all the CWAs), can be identified within about one minute, rather than the fifteen minutes allowed for AEL concentrations in traditional systems.

System Overview

FIG. 1 shows an overview of an exemplary embodiment 100 of the TeraSpec system. The TeraSpec system is capable of collecting chemical agents in the air and separating, purifying, concentrating, and analyzing the agents autonomously in a continuous fashion. In one embodiment, the response time of the TeraSpec system is less than about a minute for nearly all TICs and CWAs. In addition to the spectrometer 126, the TeraSpec system is equipped with the SSA 130, which provides advanced signal processing and noise reduction to further minimize false positives and false negatives. In one embodiment, the TeraSpec system is portable. In one embodiment, the TeraSpec system is wall-mounted. Other embodiments include various kinds of machines embodying the TeraSpec system.

This exemplary embodiment 100 of the TeraSpec system includes three major parts: the ACCS, the IAS 126, and the SSA 130. The ACCS gathers and purifies vapor samples and concentrates the chemical elements to be detected. In FIG. 1, the ACCS includes all of the components from the pre-concentrator 104 to the sonic orifice 124. In one embodiment, the ACCS also includes the sample reservoir 132 and vacuum pump 134. The IAS 126 (see FIGS. 8-20) analyzes chemical content of collected samples. In one embodiment, the IAS 126 is a rarefied pressure spectrometer, as opposed to a traditional ambient pressure spectrometer. The SSA 130 collects, analyzes, and interprets the data received from the IAS to significantly improve signal to noise ratio and the triggering of at least one alarm. The ACCS is coupled to the IAS 126. The concentrated vapor samples pass from the ACCS to the IAS 126, which measures the rotational/vibrational spectra of the vapor samples. Typically, each of the chemical agents has a unique spectral signature in the range of about 0.1 THz to 10.0 THz.

This exemplary embodiment 100 of the TeraSpec system has many advantages, including high reliability, no consumables, low maintenance, small size(e.g.,<2 cu. ft.), and light weight (e.g., <20lbs.), communication to a central monitoring system (e.g., IEEE 802.11E or Bluetooth protocol for wireless communications), autonomous operation (i.e., no human intervention), and low cost. In addition, the TeraSpec system does not destroy or modify the agents being analyzed, thereby allowing follow-up forensic analysis. The broad applicability of the THz rotational spectrum analysis can also be applied the detection of biological agents, explosive detection as part of a portal based all-threat screen system, and many other applications.

One exemplary embodiment is a method of operating the TeraSpec system. An air sample is taken from the environment 102 and drawn down a funnel into the pre-concentrator 104. The pre-concentrator 104 includes a piece of stainless steel felt or other porous filter material. Low vapor pressure materials condense on this piece of felt as the air is drawn through it by the air sampling fan 106, which has an exhaust. After air is drawn through the pre-concentrator 104 for a period of time, (i.e., the collection sample time), the pre-concentrator 104 is shut off and sealed off. Then, the pre-concentrator pump 112 draws HEPA filtered 110 air through the felt as it is heated into the concentrator 120.

The felt is heated by passing a current though it. Preconcentrated vapors 108 (or effluent) coming off the heated felt is drawn by vacuum valves 116 into the concentrator 120 and, then, cooled by a cooler 118, such as a thermoelectric cooler or rarefied (i.e., low) pressure water boiling to cool the condensing heat exchanger 114. The concentrator 120 includes the condensing heat exchanger 114, which is a sorption (i.e., adsorption and desorption) heat exchanger. The vapors are condensed again. The pressure drop through the condensing heat exchanger 114 is relatively high compared to that of the felt. Thus, there is a two-stage condensation. The first stage allows the exemplary embodiment 100 to draw air through at a relatively high flow rate so that a sample can be taken quickly and a lot of air can be sampled. The second stage, allows the exemplary embodiment 100 to get a sample in a more compact form so that the concentrated sample 128 can be introduced into the vacuum sample chamber inside the THz spectrometer 126.

After the preconcentrated vapors 108 flow into the concentrator 120, the vacuum valves 116 are closed down and the condensing heat exchanger 114 is pre-evacuated. Once most of the air is out, the condensing heat exchanger 114 is heated to a high enough temperature to drive the adsorbed molecules on the condensing heat exchanger 114 into the THz spectrometer 126, which has been pumped down to a low pressure. It is desirable to have very little air and mostly the sample in the spectrometer 126. As the pressure increases, each line in the spectra gets broader. At some point, the lines start to overlap. Thus, the sample is separated from the background air as much as possible, before entering the spectrometer 126.

The condensing heat exchanger 114 is evacuated to allow the molecules to flow into the THz spectrometer 126. At the sonic orifice 124 the molecules are further condensed before entering the THz spectrometer 126. In the spectrometer 126, a THz beam is generated, the molecules in the sample are interrogated, and a spectra is produced. The SSA 130 is a signal processing module that receives all the spectrums provided from the spectrometer 126, analyzes them, and provides the results. Then, the process repeats. The operation of this exemplary embodiment 100 of the TeraSpec is cyclical; each one is a batch process.

Figure 3:
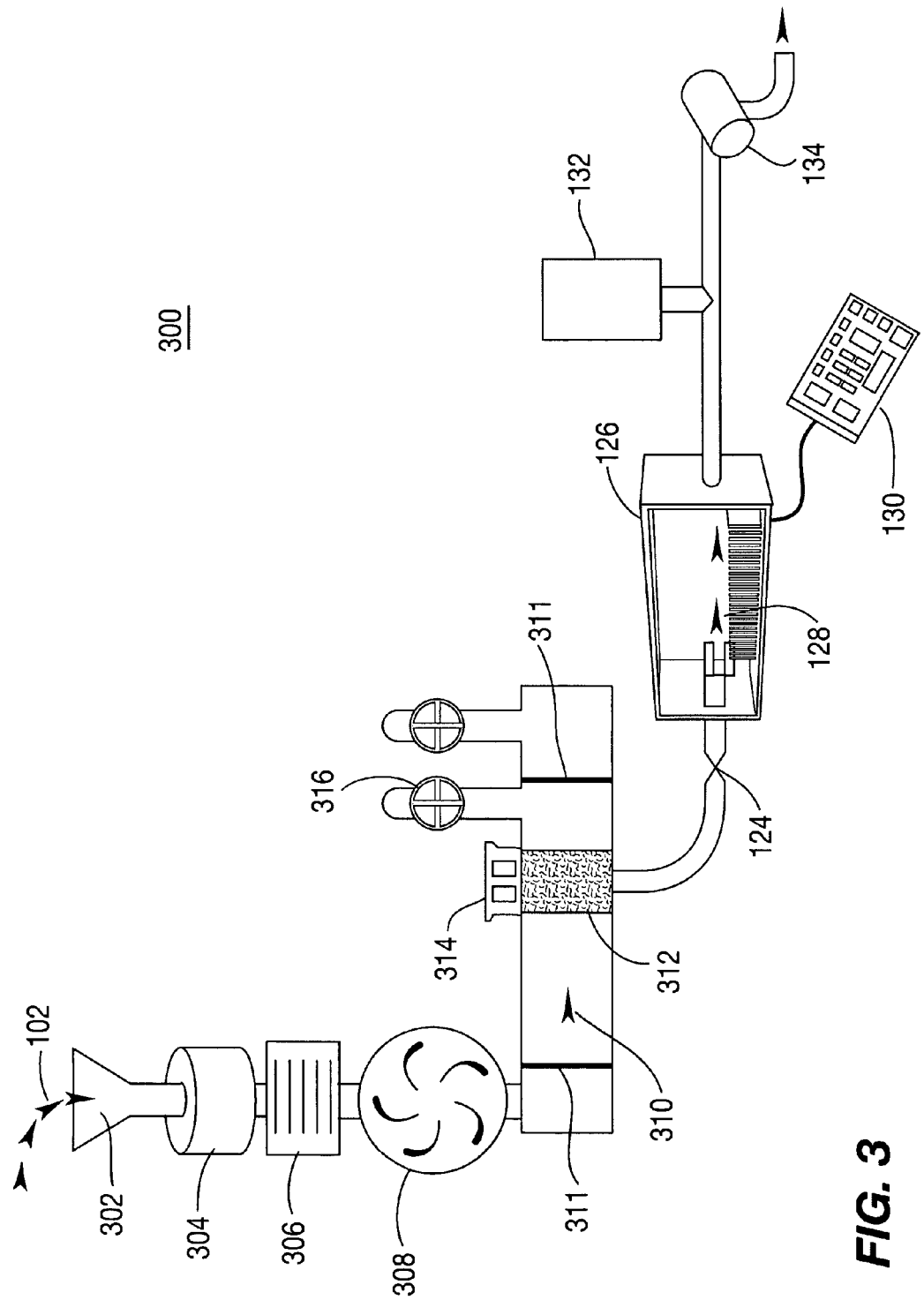
FIG. 3 is a block diagram showing an exemplary embodiment of a high vapor pressure section of a TeraSpec system.

FIG. 1 shows an exemplary low vapor pressure concentration system, as opposed to a high vapor pressure concentration system (see FIG. 3). Both low vapor pressure and high vapor pressure concentration systems employ similar sorption heat exchangers. The low vapor pressure concentration system is useful for certain kinds of chemical agents, such as trace explosives. The TeraSpec system may be configured for either high vapor pressure or low vapor pressure. The concentrator 120 is adapted for either a high vapor pressure concentration system or a low vapor pressure concentration system.

For high vapor pressure concentrator systems, it becomes difficult to concentrate the molecules, which are typically a gas. Gases must be cooled before the molecules condense on surfaces. Traditionally, cryogenic systems have been used in this case. Compression can be used instead to move up the pressure-temperature curve to get the sample to condense at temperatures, for example, just above the freezing point of water. It is desirable to prevent much water from entering the spectrometer 126, because it deleteriously absorbs radiation and skews the results. A practical way to remove water is by condensing it out. However, materials having a similar vapor pressure characteristic to water will be condensed out and fail to enter the spectrometer 126 as well. It was observed that many CWAs, TICs and other chemical agents of interest had condensation temperatures substantially above water or substantially below water. Therefore, high vapor pressure concentration systems and low vapor pressure concentration systems are defined by these observations in reference to the vapor pressure of water.

Air Collection/Concentrator System (ACCS)

One exemplary embodiment of the TeraSpec is an ACCS for sampling high vapor pressure substances and another exemplary embodiment is an ACCS for sampling low vapor pressure substances. Table 1 shows some differences between processing high vapor pressure substances and low vapor pressure substances.

TABLE 1

Differences in Processing between High and Low Vapor Pressure Agents.

| Agent Vapor Pressure | Concentration Method | Water Removal Method | Particulate Removal Method |
| --- | --- | --- | --- |
| Greater than water | Compression/Single stage condensation | Condensing gas dryer | Electrostatic precipitator |
| Less than water | Two stage condenser | Heated desorption of pre-concentrator | Particulate removed by pre-concentrator |

One exemplary embodiment of the ACCS provides the following functions for chemical detection systems. First, the ACCS collects and concentrates chemical substances of interest to improve the detection level of the TeraSpec. Second, the ACCS removes water vapor from the sample stream due to its high absorption in the millimeter wave energy in the spectrometer. Third, the ACCS provides an interface between the atmospheric pressure sample and the rarefied pressure spectrometer.

Figure 2:
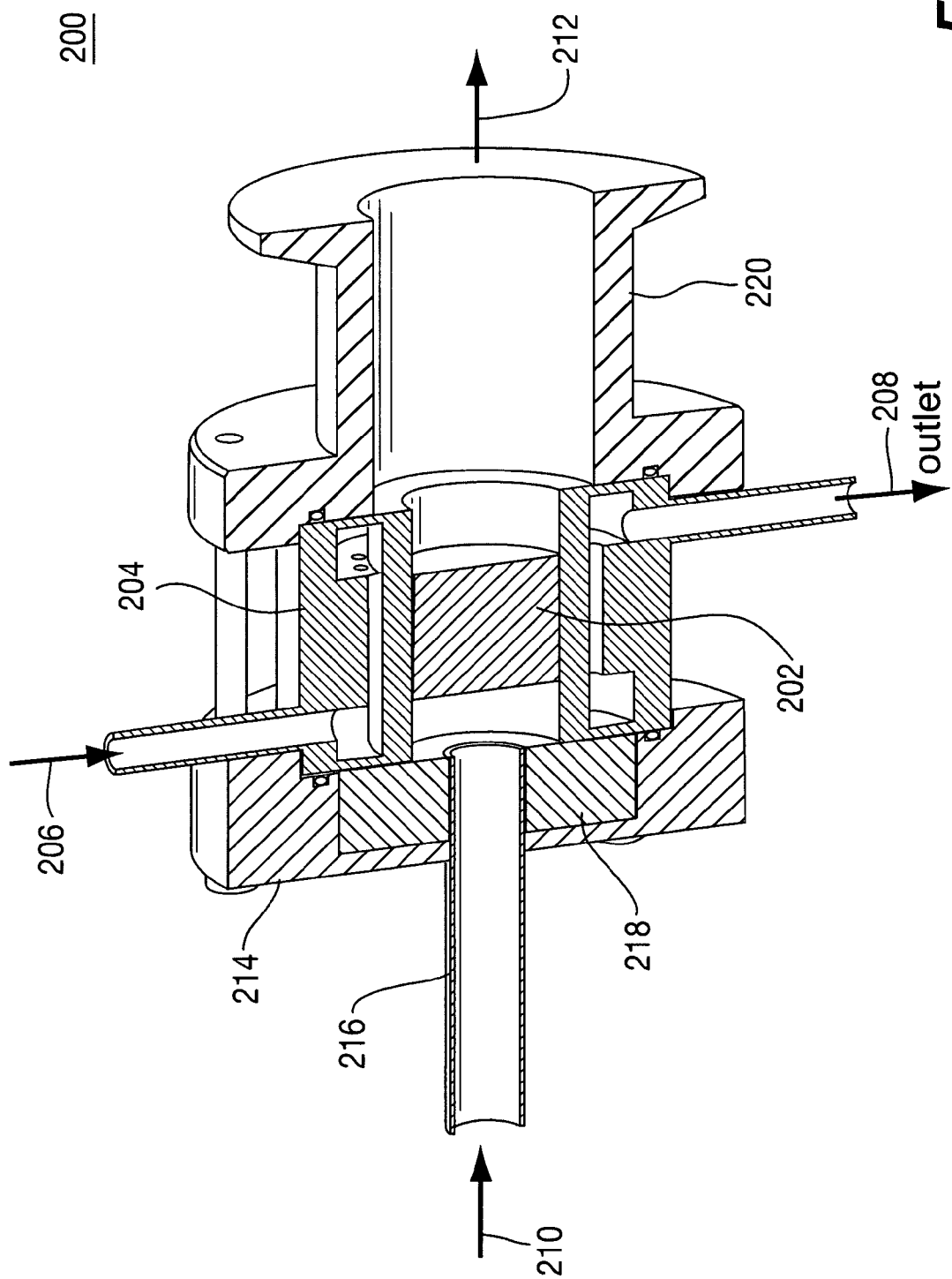
FIG. 2 is a cut away perspective view of an exemplary embodiment of a condensing heat exchanger.

FIG. 2 shows an exemplary embodiment 200 of a condensing heat exchanger, such as the condensing heat exchanger 114 in FIG. 1. This exemplary embodiment is just one of many possible embodiments. Various embodiment of the condensing heat exchanger 114 have a large surface area and a small volume and create a relatively low pressure drop so that the sample is drawn through, but with good thermal conductivity uniformly and throughout the core in order to cause not only a rapid change in temperature but a uniform change in temperature to control the sorption of the vapor being collecting. In FIG. 2, the condensing heat exchanger 114 has a radial configuration. For rapid heating and cooling and to minimize the volume of the sintered core 202, some embodiments may differ from the exemplary embodiment 200 of FIG. 2. The exemplary embodiment 200 may be used for concentrating samples of trace explosives for THz spectrometer identification, among other applications.

In FIG. 2, the sintered core 202 (e.g., a sintered nickel condenser) is part of the exemplary embodiment 200 of the condensing heat exchanger, such as the condensing heat exchanger 114 in FIG. 1. However, there is another heat exchanger, called the sample heat exchanger 204. The sample heat exchanger 204 is in contact with and outside the sintered core 202. The sample heat exchanger 204 uses water to cool the sample that is inside the sintered core 202. Other parts are around the sintered core 202. In addition, there is a water-based heat exchanger that has water inlet 206 and water outlet 208 that conductively cools the sample heat exchanger 204 by circulating water pressed inside the circular cylinder forming the condensing heat exchanger 114. This water-based heat exchanger cools the outer perimeter of the sintered core 202.

In this exemplary embodiment 200, the sample inlet 210 and heated inlet tube 216 receive the hot sample with vapors and moves it into the sintered core 202 to be condensed. The heated inlet tube 216 in coupled with some thermal insulation 214 and silicone sponge insulation 218. On the way out, through the exhaust coupling 220 and the sample outlet 212, the sample has cooled down. For example, the temperature of a sample may be 150° C. at the sample inlet 210, but 25° C. (i.e., about room temperature) at the sample outlet 212. Some components to the left of the sample outlet 212 are heated to 150° C. to avoid precondensation.

In this exemplary embodiment 200, the sample inlet 210 and heated inlet tube 216 receive the hot sample with vapors and moves it into the sintered core 202 to be condensed. The heated inlet tube 216 in coupled with some thermal insulation 214 and silicone sponge insulation 218. On the way out, through the exhaust coupling 220 and the sample outlet 212, the sample has cooled down. For example, the temperature of a sample may be. at the sample inlet 210, but. (i.e., about room temperature) at the sample outlet 212. Some components to the left of the sample outlet 212 are heated to. to avoid precondensation.

This exemplary embodiment 200 can be applied to a two-step concentration approach that is useful for extremely low concentrations of vapors emitted by concealed explosives. In this application, larges volumes of air (e.g., hundreds of liters per second) are collected from a portal that surrounding a subject of interest. The air sample is passed through a pre-concentrator 104 having a porous layer of stainless steel felt. The low vapor pressure explosive molecules readily condense on the surface of the stainless steel felt. The pre-concentrator 104 is then sealed off from the portal sampling stream and the felt is heated to desorb the explosive molecules. This effluent is subsequently drawn through a small sintered metal heat exchanger 114 that removes the heat from the gas stream thereby condensing the explosive molecules on to the surface. At the end of the condensation cycle, the sintered core 202 is sealed off, heated and evacuated into the spectrometer 126. Concentration factors in excess of seven orders of magnitude can be achieved in this manner.

One embodiment is capable of dealing with a large range of vapor pressures. Many TICs exhibit vapor pressures orders of magnitude higher than those of water, while many CWAs have vapor pressures orders of magnitude lower than those of water. Water is used as a reference material due to the necessity of removing it from the sample stream to be interrogated by the spectrometer 126. Thermally driven phase change processes provide the optimal method for the rapid removal of water vapor from a sample stream that may contain a wide variety of different substances. It is desirable to remove the maximum amount of water vapor and the minimal amount of the substances needed to be detected. The majority of the substances have vapor pressures either substantially higher than water or substantially lower. This fact has the benefit of ensuring adequate selectivity in the separation process, but requires two different approaches for affecting the water removal. Two different methods are employed for water vapor separation depending on the vapor pressure of the TIC or CWA.

FIG. 3 shows an exemplary embodiment 300 of a high vapor pressure section of a TeraSpec system. In this exemplary embodiment 300, in general, the sample compressed to a high pressure so that the sample can be condensed at a reasonable temperature by using a condensing heat exchanger 312. Air from the environment 102 enters a filter and the sample 302 is drawn into an electrostatic cleaner 304. In the first stage, the electrostatic cleaner 304 removes particulates and basically filters the sample. The second stage is the gas dryer 306 where water vapor is extracted from the sample. Water vapor is extracted from the sample by a thermal adsorption method, which is similar to a humidifier.

Then, the sample is compressed by the compressor 308 into a volume of compressed vapor 310 shown in FIG. 3 on either side of the condensing heat exchanger 312 and between a shuttle 311, which may be two pistons (shown as two black bars on either side of the condensing heat exchanger 312). During compression, the shuttle 311 starts near the sides of the condensing heat exchanger 312. Once the sample is compressed to the proper pressure, then the shuttle 311 is moved (e.g., the pistons are moved in tandem) to shuttle the sample through the sintered core 202 (see FIG. 2) of the condensing heat exchanger 312. Then, the sample is cooled and condensed. Then, the shuttle 311 moves out away from the condensing heat exchanger 312 towards the walls of the chamber containing the condensing heat exchanger 312 so that, at this point, it is similar to the low vapor pressure system (see FIG. 1). The vent valves 316 help to shuttle the compressed vapor 310 back and forth. The compressed vapor 310 is at high pressure and to keep it at high pressure it is confined to a volume.

One exemplary embodiment of the TeraSpec system for high vapor pressure substances includes a first stage that uses a compact, low-power, self-cleaning electrostatic precipitator 304 to remove particles greater than about 0.1 micron in diameter from the air stream 102. The high vapor pressure aerosolized droplets completely evaporate prior to being sampled. Thereby, the removal of particulates by this method does not reduce the sample concentration. The removal of particulates from the sampled air stream 102 greatly reduces maintenance on the micro porous vapor concentration module, i.e., condensing heat exchanger 312. The larger particles are not used in this scheme, but, in one embodiment, are directed to a secondary level analysis system, such as a microfluidic, wet chemistry based detector.

In this exemplary embodiment, the second stage uses a condensing gas dryer 306 to remove water vapor from the sample. The ability to selectively condense water vapor from the sample stream without condensing the chemical of interest is due to the very low condensation temperatures of the low vapor pressure TICs. However, this same property makes it difficult to condense the TICs in the primary condenser, i.e., condensing heat exchanger 312.

In this exemplary embodiment, compressing the sample gas stream before passing it through the condensing heat exchanger 312 raises the condensation temperature. A compressor 308 is used to sample the air 102. The sample is compressed into a cylinder located on one side of the condensing heat exchanger 312. The pressure of the sample is increased sufficiently to allow the highest vapor pressure substance to be condensed into the sintered condensing core 202 (see FIG. 2) at a temperature greater than about 0° C. Because this low temperature limit is set, ratified pressure water boiling is employed to cool the condensing heat exchanger 312. This approach allows the condensing heat exchanger 312 to be cooled very rapidly. Below this temperature range, expensive cryogens would have to be consumed to affect the cooling.

In this exemplary embodiment, the compressed sample is forced through the condensing heat exchanger 200 by a piston in the sample inlet cylinder 210 (see FIG. 2). A symmetrical outlet cylinder 212 is located on the opposite side of the condensing heat exchanger 200. The piston in the outlet cylinder 212 moves in tandem with the inlet cylinder 210 piston to maintain the proper pressure on the sample as it is condensed in the heat exchanger 200. These pistons also function to seal off the condensing heat exchanger 312 prior to evacuation into the spectrometer 126. The outlet cylinder 212 is translated back to the face of the condensing heat exchanger 312. The compressed gas in the outlet cylinder 212 is vented through a valve 316 located near the condensing heat exchanger 312. The walls of the inlet cylinder 210 are heated to prevent condensation.

One exemplary embodiment 100 (see FIG. 1) of the TeraSpec system for substances with vapor pressures lower than water (such as CWAs) is used to collect and concentrate the air sample 102. The sample is first condensed onto an ambient temperature pre-concentrator matrix 104. The pre-concentrator 104 is then sealed off and heated to an intermediate temperature while being purged with dry air to remove the desorbed water vapor. The pre-concentrator 104 is then heated to a higher temperature to desorb the remaining materials. This gas stream is drawn through a cooled heat exchanger 114 that condenses the sample. The sintered metal heat exchanger 120 is then sealed, heated and evacuated into the spectrometer 126.

One advantage of the two-stage concentrator 120 approach of this exemplary embodiment 100 is that it affords the system a method to deal with particulates and liquid droplets. It is desirable to remove all the solid particles from the sample stream to prevent clogging the micro-porous sintered core 202 (see FIG. 2) of the main condensing heat exchanger 200 that interfaces to the rarefied pressure spectrometer 126. However, inadvertent removal of chemical agent droplets by the particulate removal mechanism is a problem. Due to the low vapor pressure characteristic of most chemical warfare agents, aerosolizing is an efficient method to convert them from liquid to vapor form. These low vapor pressure droplets have relatively slow evaporation rates when compared to water. This means that the aerosolized droplets can persist in the respirable size range for a longer period. These droplets will be absorbed onto the stainless steel felt and subsequently vaporized during the high temperature desorption step. Particulates that land on the felt surface are removed by the back flushing purge used during the water desorption step.

Intracavity Absorption Spectrometer (IAS)

Figure 4:
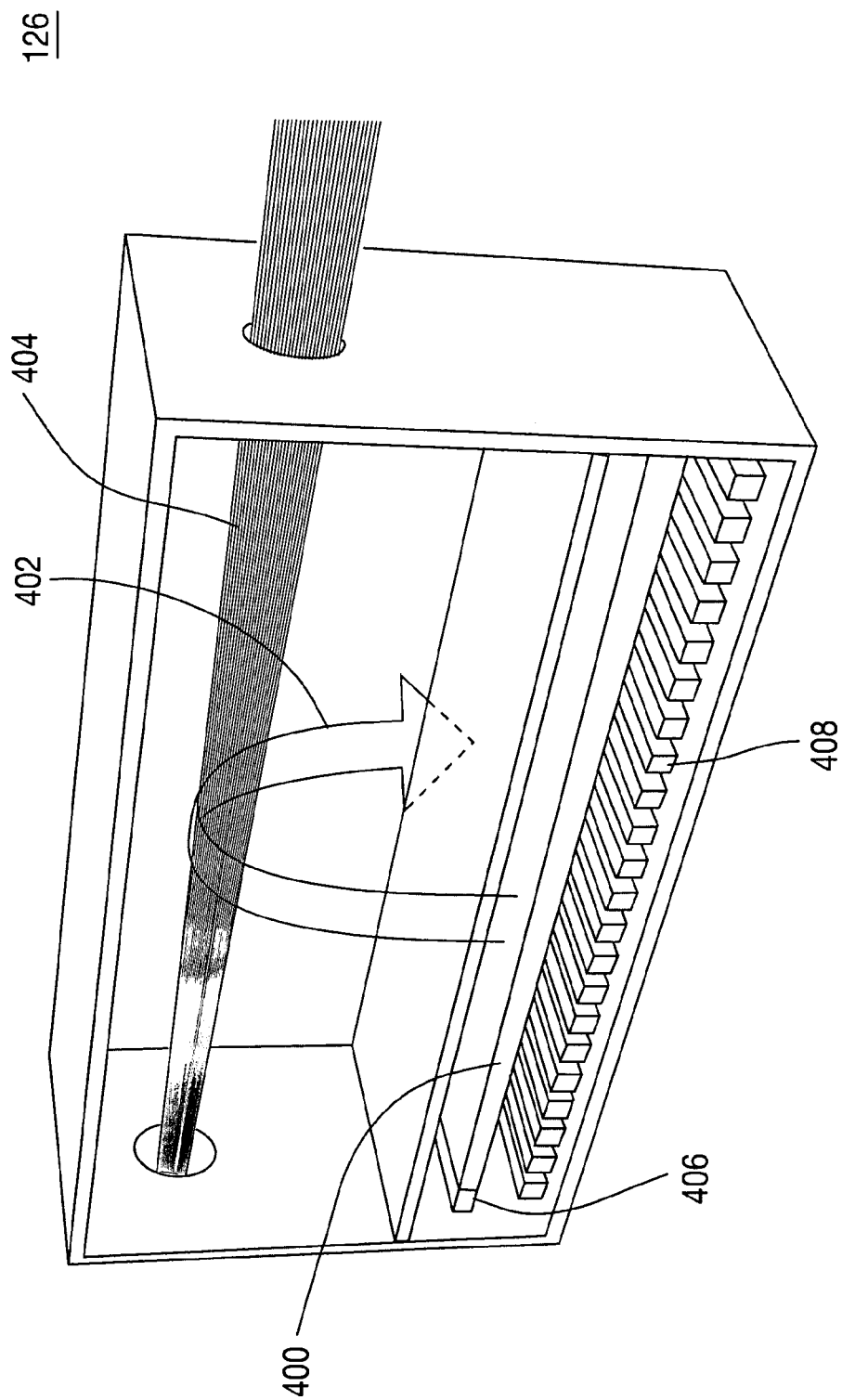
FIG. 4 is a block diagram showing an exemplary embodiment of an intracavity absorption spectrometer (IAS)

FIG. 4 shows an exemplary embodiment of an IAS 126. This exemplary embodiment is a Smith-Purcell based IAS 126 to measure the rotational/vibrational spectra of vapor samples 404. The simplest method for measuring the absorption spectrum of a sample is to tune a radiation source's frequency, allow it to pass through the sample, and measure the radiation transmitted using a sensitive detector. One embodiment combines a compact, broadly tunable, electron-beam based source of electromagnetic radiation 400 with a resonant cavity detection method that eliminates the need for a cryogenically cooled detector.

In this exemplary embodiment, the concentrated vapor sample passes from the ACCS into the IAS 126, where it is probed by a tunable source of THz radiation to measure the absorption spectrum. A rectangular-shaped cathode 406 produces a ribbon-shaped electron beam 400 with high current density that is accelerated to pass in close proximity to a conducting metallic grating 408. The interaction of the beam 400 and the grating 408 produces THz radiation 402 by the Smith-Purcell effect. The frequency of the radiation depends on the period of the grating 408, the velocity (or voltage) of the electron beam 400, and the angle at which the radiation is emitted. In this exemplary embodiment, the electrons are weakly relativistic and the radiation is emitted predominantly normal to the grating 408. The radiation passes through a THz transparent window such as silicon or mica. The radiation passes through the gas vapor sample 404 and is reflected off of the top surface of the resonator structure.

By varying the accelerating voltage of the electron beam 400, the frequency of the emitted radiation 402 is continuously tuned across the range needed to measure the absorption spectrum of the gas. To ensure high sensitivity, the resonator dimensions are tuned synchronously with the beam voltage, using a piezo-electric actuated mirror, to create a greatly increased effective path length in the device. In one embodiment, the detection process is accelerated through the use of a parallel array of IAS devices, each designed for specific spectral lines and featuring limited degrees of tuning. The feasibility of this approach will depend on the number and characteristics of spectral lines needed to unambiguously identify the presence of molecules of interest.

The rotational modes of molecules exhibit unique spectroscopic signatures. The natural frequency range for these rotational modes lies in the range from about 0.1 to 10 THz. The rotational energy states are low in energy (typically ~1 meV) so that many rotational levels are thermally populated at room temperature (kT=25 meV). Molecules can absorb electromagnetic radiation by making transitions from any thermally populated state, resulting in a substantial number of measurable lines. Rotational transitions resulting from these levels are a function of the whole molecular structure instead of a particular functional group or sub-unit of the molecule, as is the case with transitions seen using infrared spectroscopy. Also, this technique does not rely on a particular atomic composition (e.g., nitrogen content). The net result is that molecules with even slightly different structure have dramatically different rotational spectra. The absorption spectra of materials are physically fundamental and independently verifiable independent of the specific detector design. Absorption peak frequencies are constant with varying sample temperature. Lastly, by measuring the absorption spectrum at low pressure (e.g., about 10 mTorr) to minimize pressure broadening, high spectral resolution can be obtained.

IAS Design

One exemplary embodiment of the IAS 126 is comprised of an electron beam 400 and grating-loaded resonator embedded in a vacuum chamber. The beam 400 is generated with a thermionic cathode, quickly accelerated in a triode-like electrode structure, and transmitted through the anode aperture into the resonator. The electrons then drift through the resonator, gradually losing energy to the electromagnetic field. Electrons exit through a second aperture and are collected in a biased collector (Faraday cup). Sweeping this bias determines the electron velocity distribution and so indicates the degree of coupling to the field. Given that the electron energy loss is small, the Faraday cup bias is near the cathode's bias voltage; therefore much of the beam power is recovered. To maintain beam collimation, a pair of permanent magnets (1 Tesla) is placed to produce an axial guiding field approaching, in one embodiment.

One embodiment of the resonator, in its simplest form, is a planar-confocal geometry with axis-oriented perpendicular to the electron beam 400. The planar reflector is periodically grooved to allow coupling with the electrons through a particular spatial harmonic of the electromagnetic mode traveling with the electron velocity. Since this velocity is lower than that of radiation, the harmonic field is bound to the grooved surface and so the electron beam 400 must pass within this bounding region. This is a constraint on the quality of the beam necessary to operate at a given frequency. More sophisticated geometries, such as a Grating Horn where the planar reflector is folded around the beam (i.e., a V-shaped structure where the e-beam is located just above the intersection of the V), enhance the coupling dramatically, in one embodiment. Coarse tuning of the resonant frequency is achieved by varying the electron velocity while the distance to the spherical mirror provides fine-tuning. By mounting the mirror on piezo-electric actuators, very high resonator quality is maintained with real-time frequency sweep capability, in one embodiment. Likewise, the velocity is swept quickly as well to give broad flexibility in one embodiment.

The electron beam 400 degrades with increasing pressure. Therefore, in one embodiment, a window transparent to the resonant frequency bisects the resonator so that the beam 400 occupies one region and the other is filled with the target molecular gas injected into the resonator for inspection. The beam region is maintained at low pressure, e.g., 10-6 Torr for tungsten or 10-7 Torr for LaB6 cathodes. The gas pressure is controlled by the size of the inlet nozzle and outlet aperture or valving, in some embodiments. Care is taken so that the gas does not cloud the window or mirror, thereby degrading the resonator. To avoid this, either the gas is injected as a jet directed at the outlet or layers of inert buffer gas flow over these surfaces, in some embodiments.

One advantage of the IAS 126 is that it is a simple detection scheme. The presence of a resonant absorber in the cavity affects the electron beam coupling, which is reflected in the velocity distribution at the Faraday cup. Detecting the absorber is achieved by measuring the collected current with microampere resolution, while sweeping the Faraday cup bias. Known targets are regularly injected into the IAS to provide a calibration standard, in some embodiments.

In one embodiment, the resonator dimensions are roughly 5 cm on a side and roughly 2 cm wide. To measure a series of lines, an array of individually tuned resonators is placed side by side within the same vacuum chamber for some embodiments that have a size constraint.

Spectral Signature Analyzer (SSA)

Figure 5:
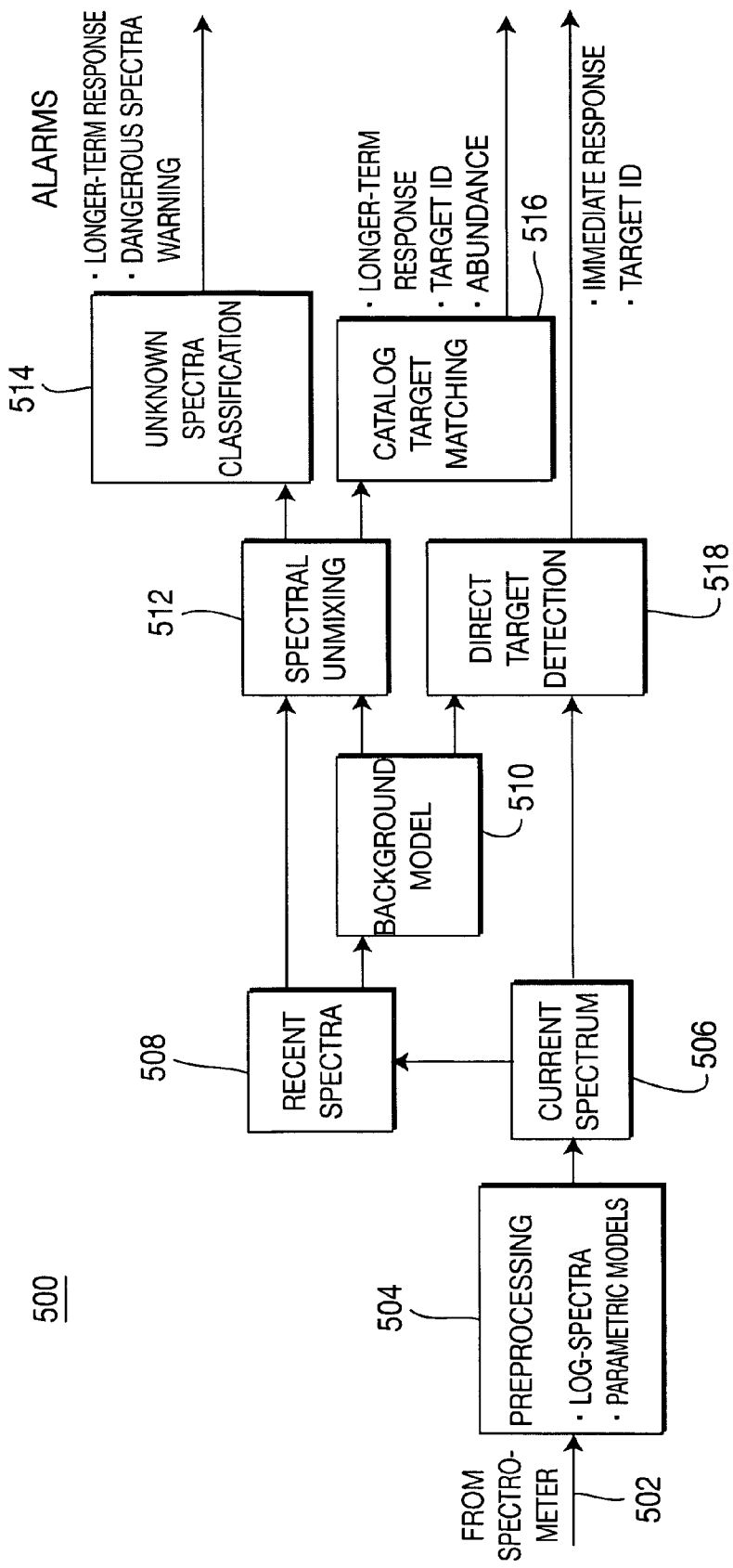
FIG. 5 is a flow chart showing an exemplary embodiment of a method of the spectral signature analyzer (SSA)

FIG. 5 shows an exemplary embodiment 500 of a method of the SSA 130 of FIG. 1. Software for the SSA 130 performs approximately real time analysis on the THz spectra. One purpose of the SSA 130 is to separate the spectra of background chemicals from those of the CWAs and TICs.

In this exemplary embodiment 500, at 504, a preprocessor overcomes the nonlinear nature of spectral absorption by taking the logarithm of the measured spectra 502. If the signal-to-noise ratio is low, the measured log-spectrum is regularized using a parametric model. At 518, an immediate response target detector is optimized for each known CWA or TIC. Statistically optimal detectors are chosen to use the current 506, target 508, and background 510 spectral signatures. In order to accommodate a dynamically changing background, the detectors perform adaptive modeling of the background at 510.

In order to provide both abundance information and higher confidence detection results, spectral unmixing is performed at 512 to extract all the sources, using a collection of measured spectra over an extended time period. Because extensive THz spectra catalogs do not exist, an unmixing algorithm is used that is capable of simultaneously extracting the abundances and source spectra, without requiring prior knowledge of the materials present. The extracted sources are then matched at 516 to known CWAs and TICs. To allow for the possibility of unknown CWAs or TICs, unknown spectra in large abundance are then classified at 514 by a previously trained neural network as either benign or potentially dangerous.

If the false alarm rate is still unacceptably high, a novelty detector is added as a first stage, in one embodiment. The novelty detector looks for an abrupt change in the measured spectrum alone relative to its recent past. The advantage of this approach is that it obviates the need for continual identification of all gases by allowing slow changes in the background spectra due to drift of humidity, dust, pollen, and pollution levels, many of which vary as diurnal cycles. Thus, unknown gases can enter the system without triggering an alarm, as long as their concentrations change very slowly.

Preprocessing

The first step in detecting target spectral signatures is to linearize the problem. Because the measured spectrum is the product of the individual spectra, which in turn depends non-linearly on the individual spectra and abundances, taking the logarithm converts the product into a sum and linearizes the mixed spectra:

$$z(\lambda) = I(\lambda) \prod_{m=1}^{M} \exp(-a_m s_m(\lambda))$$

becomes $$\log[z(\lambda)] = \log[I(\lambda)] - \sum_{m=1}^{M} a_m s_m(\lambda)$$

Here, $z(\lambda)$ is the measured spectrum at wavelength $\lambda$, $s_m(\lambda)$ is the spectral absorption of material m at wavelength $\lambda$, $a_m$ is the relative abundance of material m, and $I(\lambda)$ is the intensity of the probing THz radiation.

The use of parametric models is investigated for the measured spectra. Parametric models have the potential to reduce sensor noise; however, they must be chosen carefully. If the models are a poor match to the underlying physics, or have too few adjustable parameters, they may hide important features in the spectra. On the other hand, if they have too many free parameters, they will simply recreate the original spectrum. Auto-regressive (AR) spectral models are good at modeling absorption nulls.

Target Detection and Identification

The detection algorithms are divided into two classes: those that directly detect the target of interest using only a single spectrum measurement and those that attempt to unmix the spectra from several measurements and then match the constituent source spectra to a catalog.

Direct Target Detection

The spectral signature of a known CWA or TIC can be detected within a single spectrum measurement, as long as the signal to noise (background) ratio is not too large. The classical approach is to monitor the likelihood ratio between the hypothesis that the target is present versus the hypothesis that the target is absent. If this likelihood ratio exceeds a threshold, then an alarm is triggered. Depending on the statistical assumptions, this leads to several closely related algorithms such as the generalized likelihood ratio test (GLRT), the adaptive matched filter (AMF), and the adaptive coherence estimator (ACE). Common to all these algorithms is a test statistic $d(x, m_x, \Sigma_x, s_t)$ that is a function of the current spectra, x, the target spectra, st, and a background model parameterized by its mean and covariance $(m_x, \Sigma_x)$. The background model is estimated adaptively using a buffer of recently collected spectra. The size of this buffer is important. If it is too short, the statistical model itself will have a large variance, increasing the chance that an incoming spectrum will deviate from the model and trigger a false positive. On the other hand, if this window is too long, the model will incorporate variations in the spectrum that can occur over time, and therefore will err on the side of missing significant events, thus generating false negatives.

In addition to detecting the target of interest, subspace detection methods build a more discriminative detector by explicitly suppressing other signals. In this case, the test statistic has the form $d(x, S_t, s_t)$, where $S_t$ is a matrix containing other target signatures.

Indirect Target Identification

Another approach to target detection is to make use of repeated spectra measurements over time to unmix the total spectrum into its constituent spectra and their relative abundances, and then determine if there is a match between the source spectra and the agent catalog. A match is determined by measuring the distance from the constituent spectra to each entry in the catalog using a standard metric, such as spectral angle mapping or spectral correlation. If one of the distances to a dangerous material entry is less than a predefined threshold, a match is deemed to occur, and an alarm is triggered.

After preprocessing, the mixture equation can be written as X=AS+N, where $X(x_{\tau\lambda})$ is a matrix of the log-intensity at frequency λ measured at time τ, $S(s_m\lambda)$ is a matrix of the spectrum of the $m^{th}$ material at frequency λ, and $A(a_{\tau m})$ is a matrix of the relative abundance of material m obtained during measurement at time τ. The noise term $N(n_{\tau\lambda})$ accommodates modeling errors and sensor noise, as well as the residual intensity term.

If there is sufficient diversity in the spectral measurements, meaning each measurement cycle measures a slightly different mixture of the constituent materials, then the abundances can be recovered using a least squares solution: $A=(S^TS)^{-1}S^TX$. A better solution adds the constraint that the abundances at each time must be non-negative and sum to one. However, this solution requires prior knowledge of the materials actually present.

Figure 6:
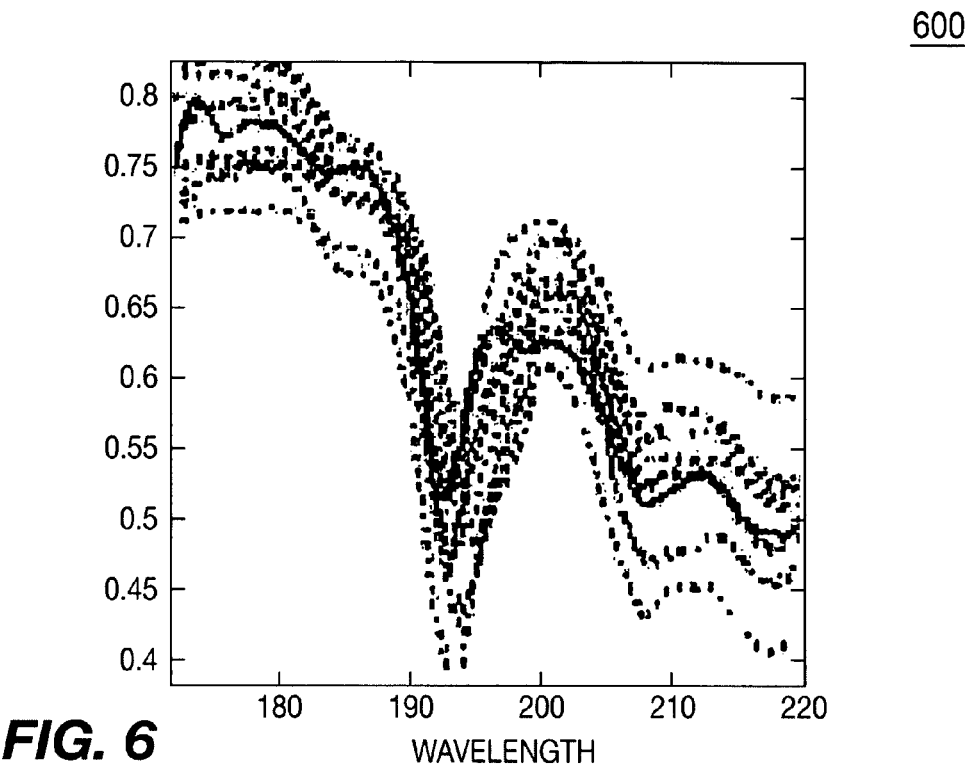
FIG. 6 shows an example of spectra matching.

Alternatively, an unmixing algorithm discovers the abundances and spectra together without the requirement of a source catalog. The algorithm starts with a probabilistic model for the joint distribution of the abundances and source spectra expanded using Baye's law: $p(A,S|X)=p(X|A,S)p(A,S)|p(X)$. It then finds the optimal value of the abundances and spectra using maximum a posterior (MAP) optimization: $\{A_{map}, S_{map}\}$=arg max $p(A, S|X)$. One key to making the algorithm robust is to use intelligent priors about the general shape of spectra, the relative abundances, and the distribution of the noise. These priors, when combined with the MAP procedure, lead naturally to independent component analysis (ICA). While principal component analysis (PCA) is often used to find uncorrelated sources, ICA is a more powerful algorithm that finds statistically independent sources. Once the source spectra have been extracted, the classical techniques for matching the unknown spectra to the agent catalog can be used, such as spectral angle mapping (SAM) and spectral correlation mapping (SCM). FIG. 6 shows an example of spectra matching. The problem with this approach in the context of the current system is that it requires a long time period to collect enough data to perform the unmixing. Specifically including as a prior the spectra of gases known to be always present, such as air, could reduce this time.

Unknown Spectra Classification

If it is determined that an unknown spectra is present in significant abundance, but it is not in the catalog of known CWAs and TICs, then the spectral classification stage is triggered. Under the assumption that many dangerous gases will have some common elements to their spectra, a classifier can be trained to distinguish between benign and dangerous spectra. Many classifiers can be used for this purpose, but when the signal to be classified has a large dimension (in this case, frequency) but few training exemplars, then support vector machines (SVM) are the classifier of choice.

Feedback to Spectrometer

If a detection is made but the decision statistic is close to a threshold, a request can be made to the spectrometer to rescan the gas at a greater resolution in certain critical parts of the frequency spectrum, such as near absorption bands, to increase the confidence level of detection.

Novelty Detector

If the false alarm rate is unacceptably high in the previous approach, we intend to add a novelty detector as the first stage in the algorithm. The novelty detector monitors the evolution of the background spectrum alone for abrupt changes. If a change occurs too rapidly, then it will trigger the next stage, which then attempts to identify the source of the change. The algorithm bootstraps itself through a self-calibration period, when it is known that there are no CWAs or TICs present. During this period, multiple spectra are accumulated and a model of their statistical distribution establishes a baseline. Then, when a new spectrum is obtained, it is tested for deviation from the distribution of the baseline spectra. If it is larger than some threshold, then the source identification stage is invoked. One common test statistic is the Mahalanobis distance, $$d^2 = (x - m_x)^T \sum_x^{-1} (x - m_x),$$

between the incoming spectra, x, and an assumed Gaussian distributed background spectra with mean and covariance $(m_x, \Sigma_x)$. This test statistic is a constant false alarm rate (CFAR) detector. However, we may consider other test statistics as well. If this test fails, then the most recent spectra, x, is absorbed into the background statistical model, $(m_x, \Sigma_x)$, while the oldest spectra is discarded from the model. In this way, the baseline model is always calculated using a temporal window of the most recent past. In addition to monitoring the total spectrum for changes relative to its recent past, monitoring for changes relative to the same time in the diurnal cycle, again collected within a window of the recent past, but at the same time of day is performed in one embodiment.

Sample Storage

A series of reservoirs to collect CWA/TIC for future laboratory analyses will be provided at the output end of the SP spectrometer 126 as shown in FIG. 1. A T-valve isolates the reservoirs from the pump. When an agent is detected, the T-Valve switches the flow towards the first reservoir. Any subsequent CWA/TIC agents detected will be captured in next reservoir in queue. The full reservoirs can be taken to the laboratory for further testing.

Wireless Communication

Ad-hoc wireless sensor network technology based on open standards (e.g., Bluetooth and IEEE 802 11 b) is used to interconnect the sensors. Alarms, maintenance information and status reports are automatically transmitted to control stations. Though designed for autonomous operation by a single node, this feature allows several sensors to collaborate; for example, a sensor alert at one sensor may be used by another to anticipate an attack by a sensor elsewhere in the system.

Figure 7:
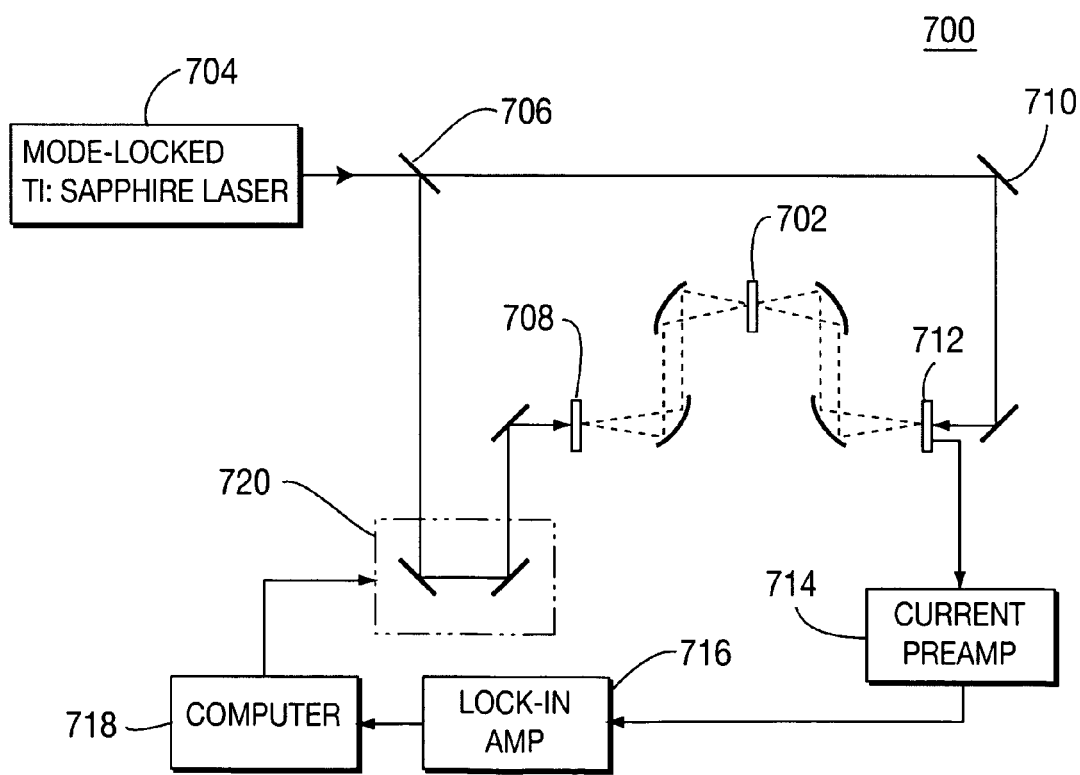
FIG. 7 is a block diagram showing an exemplary embodiment of an IAS.

FIG. 7 shows an exemplary embodiment 700 of an IAS. In this embodiment 700, the spectrometer is a time-domain THz spectrometer, such as a mode-locked semiconductor laser. In a further embodiment, the spectrometer can measure the transmission or reflection of solid, gas, or liquid samples in the range of about 0.1 to 2.0 THz. The spectral resolution can be as small as about 0.01 THz. The spectrometer includes Argon Ion lasers that optically pump a mode-locked Ti:Sapphire laser 704. The Ti:Sapphire laser 704 operates at about 800 nm with about 100 fs pulses at a repetition rate of about 100 MHz. The infrared light is split into two beams by a beam splitter 706. One beam is directed onto a microfabricated THz antenna, transmitter 708, fabricated on Low Temperature grown Gallium Arsenide (LT-GaAs). The generated THz radiation is a subpicosecond pulse of THz radiation with energy predominately in a range of about 0.1 to 2.0 THz. The THz radiation is collimated and focused using a set of four parabolic mirrors 710. After passing through (or reflecting) from a sample of interest, the THz radiation is focused on a second THz antenna, receiver 712. The second beam from the Ti:Sapphire laser 704 gates the detection antenna 708 to produce a signal proportional to the instantaneous amplitude of the THz electric field. By delaying the arrival of the THz signal with respect to the gating laser pulse, the THz electric field as a function of time can be measured. Standard Fourier Transform algorithms can be applied to the time-domain waveforms to extract the amplitude and phase of the THz electric field as a function of THz frequency. The THz spectral resolution is determined by the total time delay 720 recorded.

A method and apparatus are provided for the detection of terahertz radiation absorption by a target to indicate the presence of contaminants. A source of coherent far infrared radiation is used in conjunction with a detection system to facilitate a convenient and effective method of performing frequency modulation spectroscopy in the far infrared spectrum.

Figure 8:
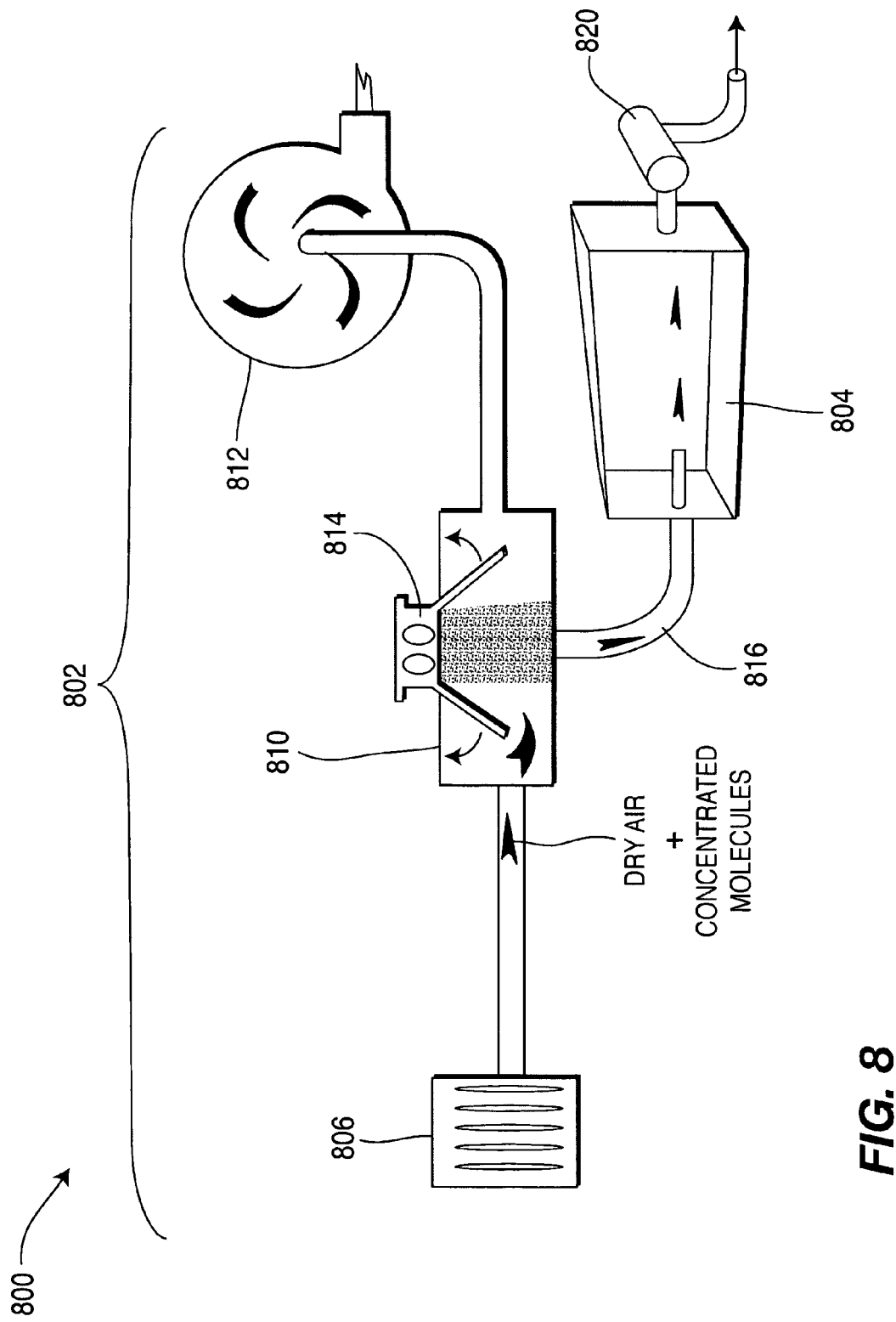
FIG. 8 is a block diagram illustrating a perspective view of one embodiment of a system 800 for concentrating and analyzing a sample for the detection of contaminants such as explosives.

FIG. 8 illustrates a perspective view of one embodiment of a system 800 for concentrating and analyzing a sample for the detection of contaminants such as explosives. The system 800 comprises a concentrator 802 and a terahertz detection system 804. The concentrator 802 is coupled to the detection system 804 to provide a concentrated sample to the detection system 804 for analysis. Concentrating the sample allows the detection system 804 to work more effectively because the vapor densities of most contaminants of interest (e.g., explosives or other chemicals) are on the order of parts per trillion and would therefore be otherwise difficult to detect in a diluted sample.

The concentrator 802 comprises a pre-concentrator 806, a dryer 808, a heat exchanger 810 and a sampling pump 812. The pre-concentrator 806 is adapted to heat a sample in gaseous or liquid form and boil off contaminant vapor molecules from the rest of the sample. The pre-concentrator 806 is coupled to the dryer 808, which combines the contaminant vapor molecules with a transport medium and passes the vapor molecules to the heat exchanger 810. In one embodiment, the transport medium is an inert gas. The heat exchanger 810 is adapted to condense the contaminant vapor molecules, which are then drawn out of the heat exchanger 810 and through the detection system 804 for analysis.

The heat exchanger 810 is adapted to be cooled so that the contaminant vapor molecules received from the dryer 808 condense on an interior surface of the heat exchanger 810. In one embodiment, the heat exchanger 810 is adapted to be cooled for a pre-determined interval of time to allow a quantity of vapor molecules to condense. The heat exchanger 800 is further adapted to be sealed and heated to evaporate the vapor molecules that absorbed onto the interior surface of the heat exchanger 810. The heat exchanger 810 is then evacuated by a pump 820 that is coupled to the detector system 804 to draw the contaminant vapor molecules through the detector system 804. In one embodiment, a sonic orifice 816 couples the heat exchanger 810 to the detection system 804 to control the pressure within the detection system 804. The heat exchanger 810 is designed to have minimal pressure drop in the ambient pressure vapor flow direction.

In one embodiment, the heat exchanger 810 is cooled by a thermal electric cooler 814 during the condensation phase. By reversing the thermal electric cooler 814, the heat exchanger 810 may be heated for the evaporation phase. In another embodiment, electrical resistance heaters are used in combination with the thermal electric cooler 814 to facilitate evaporation. In another embodiment, the heat exchanger 810 is cooled by rarified pressure water boiling. This approach allows the heat exchanger to be cooled very rapidly.

Figure 9:
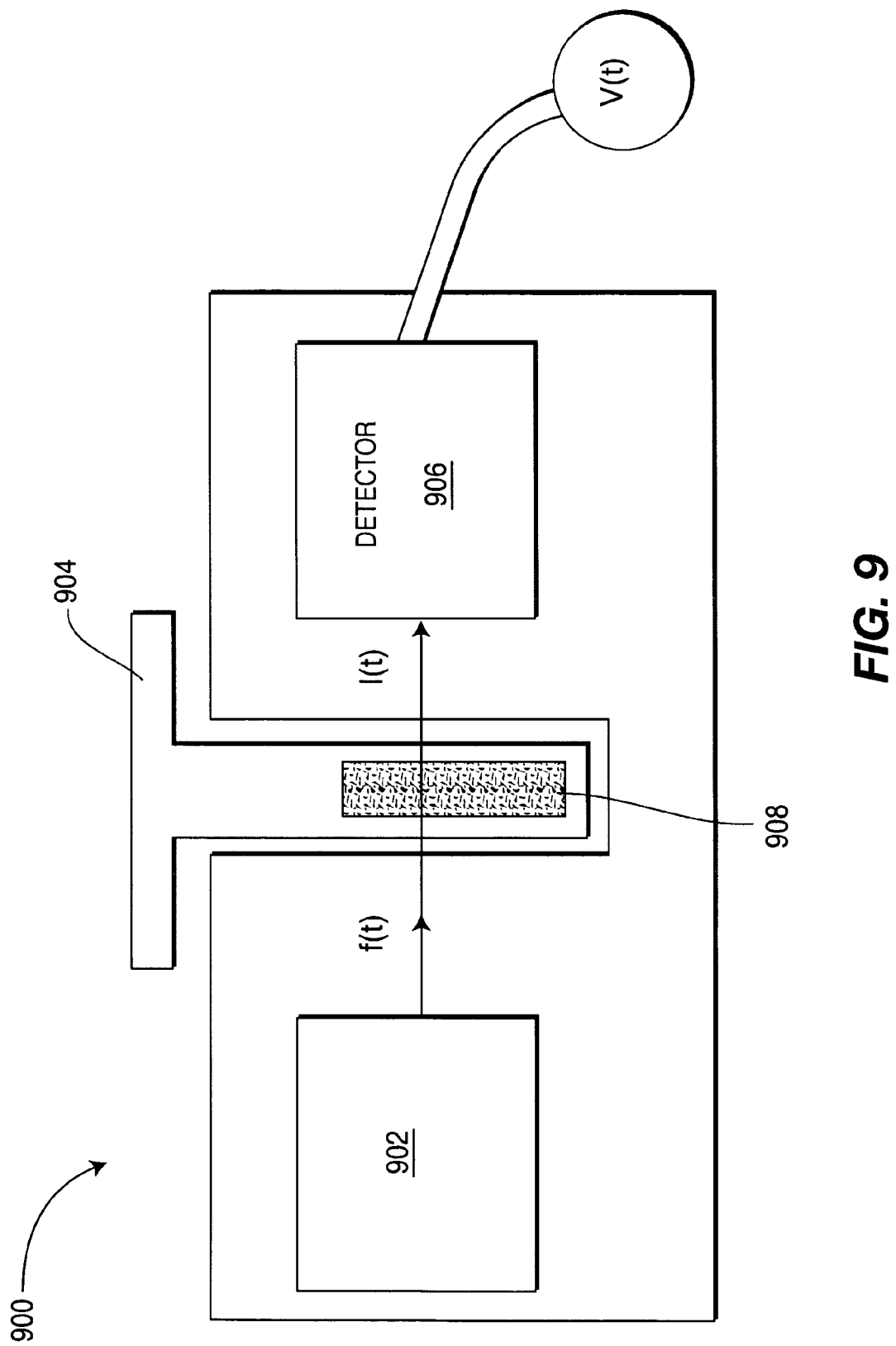
FIG. 9 is a block diagram illustrating a perspective view of one embodiment of a detection system 900 for detecting terahertz radiation absorption by a sample.

FIG. 9 illustrates a perspective view of one embodiment of a detection system 900 for detecting terahertz radiation absorption by a sample 908 (e.g., a low-pressure gas). The system 900 is a turn-key spectrometer maintained at a vacuum and comprises a radiation source 902, a cell 904, and a detector 906. The radiation source 902 provides frequency modulated output (i.e., terahertz radiation) f(t) to the cell 904. The output f(t) passes through the sample 908, which is contained within the cell 904, and molecules in the sample 908 may absorb some frequencies of light from the source output f(t), depending on the nature and quantity of chemical and/or biological agents present within the sample 908. Consequently, the intensity of the light that entered the cell 904 decreases and an intensity modulated beam of light I(t) exits the cell 904. The intensity modulated beam I(t) passes into the detector 906, which registers a voltage V(t) that may be used to calculate the intensity differential of the emitted radiation across the cell 904.

In one embodiment, the radiation source 902 is a far infrared swept source. The cell 904 has far infrared transmissive walls to allow the frequency modulated source output f(t) and the intensity modulated beam I(t) to pass therethrough. In one embodiment, the detector 906 is a broadband detector.

Figure 10:
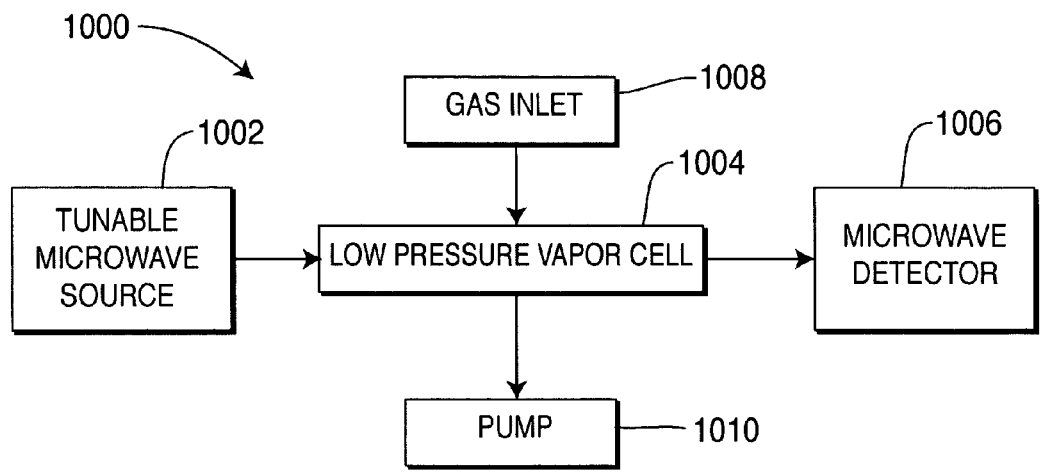
FIG. 10 is a block diagram illustrating a schematic diagram of one embodiment of a solid state detection system for detecting terahertz radiation absorption by a sample.

FIG. 10 illustrates a schematic diagram of one embodiment of a solid state detection system 1000 for detecting terahertz radiation absorption by a sample (e.g., a low-pressure gas). The system 1000 is contained within a vacuum and is similar to the spectrometer 900 illustrated in FIG. 9; however, the system 1000 may be particularly advantageous in detecting the presence of explosives such as TNT or DNT, among others. The system 1000 comprises a tunable microwave source 1002, a low-pressure vapor cell 1004 and a microwave detector 1006. The microwave source 1002 is coupled to the vapor cell 1004 so as to pass radiation in the far infrared spectrum through the vapor cell 1004. The vapor cell 1004 is also coupled to the detector 1006, which is positioned to detect the frequencies of light that exit the vapor cell 1004 (i.e., the frequencies that are not absorbed by molecules in the sample). A gas inlet 1008 is coupled to the vapor cell 1004 to provide the sample to the system 1000. In one embodiment, the gas inlet is similar to the sonic orifice 816 illustrated in FIG. 8. A pump 1010 is also coupled to the vapor cell 1004 to maintain a low pressure differential, and in one embodiment, the pump 1010 is similar to the pump 820 illustrated in FIG. 8.

In one embodiment, the microwave source 1002 is an IMPATT multiplier whose input is low frequency microwaves produced by a solid state oscillator. The low range of frequencies at which the microwave source 1002 operates makes it ideally suited for the detection of explosives such as TNT or DNT, which have peak rotational absorptions in the low terahertz range. In another embodiment, the microwave source 1002 is a far infrared swept source. Furthermore, the production of a range of frequencies by the microwave source 1002 allows the detector 1006 to observe variations in the absorption of the sample with frequency, which enables more accurate identification of explosives. In one embodiment, the detector 1006 is cryogenically cooled to detect the decrease in signal of the radiation that passes through the sample in the vapor cell 1004.

Figure 11:
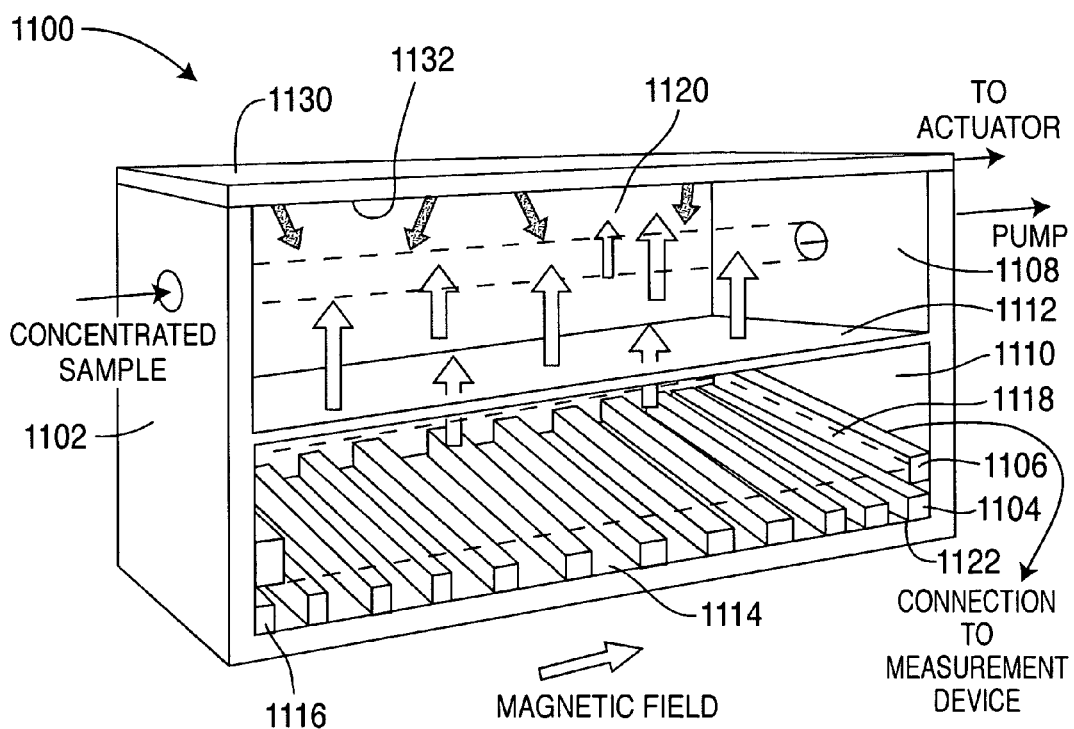
FIG. 11 is a block diagram illustrating a perspective view of an embodiment of a detection system for detecting terahertz radiation absorption by a sample.

FIG. 11 illustrates a perspective view of an embodiment of a detection system 1100 for detecting terahertz radiation absorption by a sample. The system 1100 comprises a microwave cavity 1102, a grating 1104 and a collector 1106. The microwave cavity 1102 further comprises a lid 1130 and a terahertz transmissive window 1112 that splits the microwave cavity 1102 into two regions: a sample chamber 1108 and a vacuum chamber 1110. The lid 1130 has a reflective surface 1132 that is positioned to face the transmissive window 1112. The grating 1104 is positioned on a flat surface 1114 of the vacuum chamber 1110 that faces the window 412. The collector 406 is positioned at a second end 1116 of the grating 1104.

A concentrated sample gas is provided to the sample chamber 1108, for example via sonic orifice 816 (FIG. 8), for analysis. Sample analysis is facilitated by exploiting a phenomenon known as Smith-Purcell radiation. When an electron beam 1118 is passed close to the grating 1104 from a first end 1116 to a second end 1122, the beam 1118 is "bunched" by the grating 1104, and light waves 1120 are generated that propagate at an angle substantially normal to the electron beam 1118. The light waves 1120 pass through the window 1112 and into the sample chamber 1108, where the light waves encounter the reflective surface 1132 of the lid 1130. The reflective surface 1132 discretizes the light waves into bands. A magnetic field having lines substantially parallel to the electron beam 1118 acts on the beam 1118 and bends the path of the beam 1118 approximately when the beam 1118 reaches the second end 1122 of the grating 1104.

As discussed herein with reference to FIGS. 9 and 10, some frequencies of the emitted light 1120 may be absorbed by molecules in the sample gas. Absorption of frequencies will cause the electron beam 1118 to lose energy. The more energy that is lost by the electron beam 1118, the more the beam 1118 will bend. The collector 1106 intercepts the electron beam, and a measurement device coupled to the collector 1106 receives information from the collector to determine the amount of energy lost by the electron beam. Specifically, the information intercepted by the collector 1106 demonstrates the degree to which the electron beam 1118 bends (i.e., the locations at which the beam 1118 hits the collector 1106) and the energy of the beam 1118 after it passes over the grating 1104 (i.e., how much current hits the collector 1106) for a particular emitted frequency. Thus, the absorption of the light 1120 at a particular frequency can be indirectly measured by performing energy spectroscopy on the electron beam 1118 (i.e., by determining the amount of energy lost by the beam 1118).

The system 1100 is tunable by varying the voltage of the electron beam 1118. That is, the frequency of the light waves 1120 emitted by passing the electron beam 1118 over the grating 1104 is a function of the grating period (i.e., spacing of the grating 1104) and the voltage of the electron beam 1118. Thus, the system 1100 is tunable over a spectrum of terahertz frequencies to facilitate accurate detection of contaminants in a sample. In another embodiment, the lid 1130 may be coupled to an actuator to alter the position of the reflective surface 1132, so that the bands of discretized light reflected by the reflective surface 1132 can be controlled.

Figure 12:
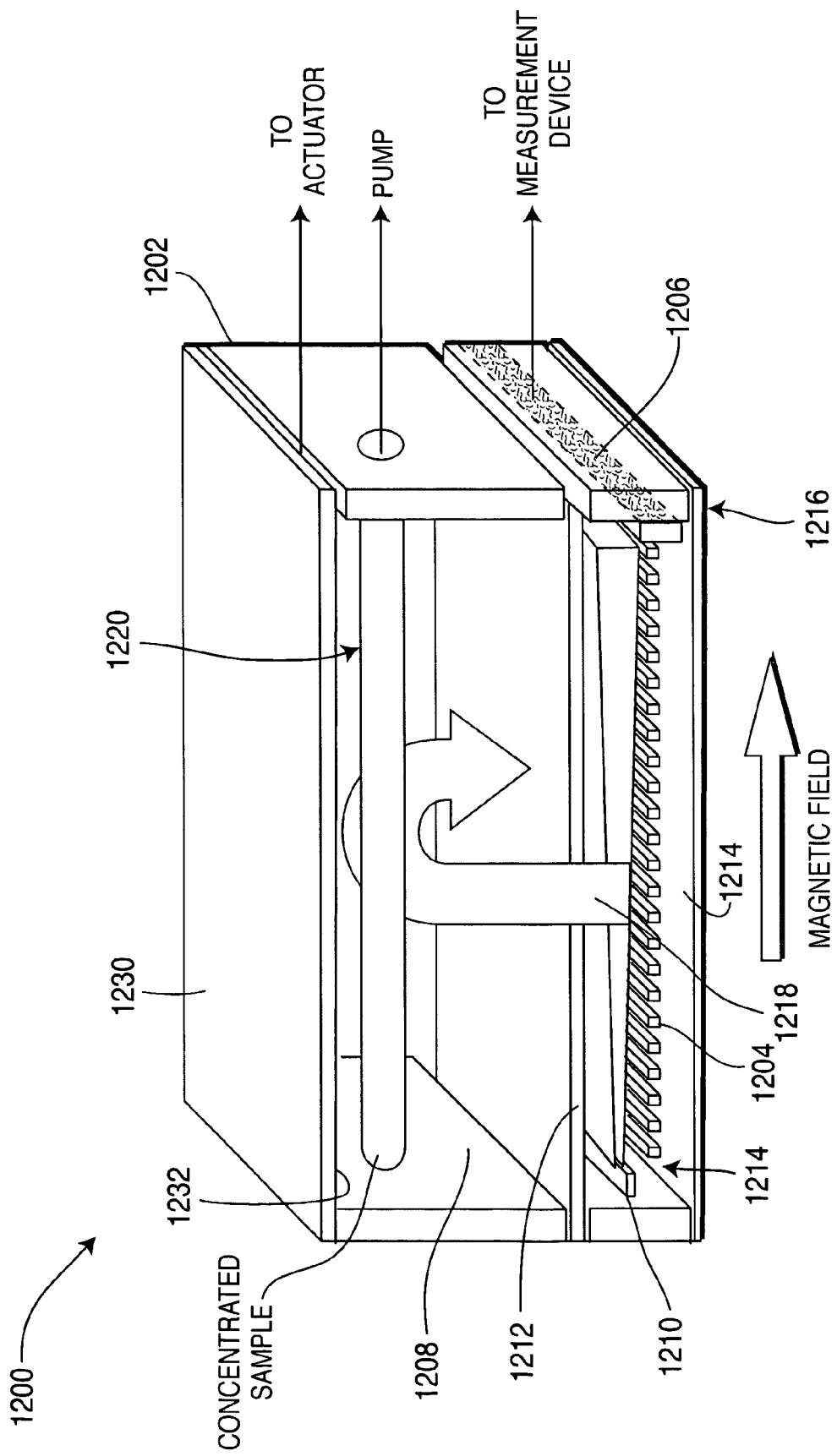
FIG. 12 is a perspective view of an embodiment of a detection system for detecting terahertz radiation absorption by a sample in which the sample is suspended in a liquid rather than a gas.

FIG. 12 is a perspective view of an embodiment of a detection system 1200 for detecting terahertz radiation absorption by a sample in which the sample is suspended in a liquid rather than a gas. The system 1200 is substantially similar to the system 1100 illustrated in FIG. 11 and comprises a microwave cavity 1202, a grating 1204 and a collector 1206. The microwave cavity 1202 further comprises a lid 1230 and a terahertz transmissive window 1212 that splits the microwave cavity 1202 into two regions: a sample chamber 1208 and a vacuum chamber 1210. The grating 1204 is positioned on a flat surface 1214 of the vacuum chamber 1210 that faces the window 1212. The collector 1206 is positioned at one end 1216 of the grating 1204, opposite the point of entry for an electron beam. The lid 1230 has a reflective surface 1232 positioned to face the transmissive window 1212.

A sample tube 1220 spans the sample chamber 1208 and is positioned substantially parallel to the grating 1204. A sample for analysis is concentrated within a liquid that is contained within the sample tube 1220. When an electron beam is passed close to the grating 1204 from a first end 1214 to the second end 1216, the beam is "bunched" by the grating 1204, and light waves 1218 are generated that propagate at an angle substantially normal to the electron beam. The light waves 1218 pass through the window 1212 and into the sample chamber 1208, where the light is discretized into bands by the reflective surface 1232 of the lid 1230. A magnetic field having lines substantially parallel to the electron beam acts on the beam and bends the path of the beam approximately when the beam reaches the second end 1216 of the grating 1204.

As discussed herein with reference to FIG. 11, some wavelengths of the emitted light may be absorbed by molecules in the sample contained within the sample tube 1220. Absorption of wavelengths will cause the electron beam to lose energy, and the more energy that is lost by the electron beam, the more the beam will bend. The collector 1206 intercepts the electron beam, and a measurement device coupled to the collector 1206 receives information from the collector to determine the amount of energy lost by the electron beam. Specifically, the information intercepted by the collector 1206 demonstrates the degree to which the electron beam bends (i.e., the locations at which the beam hits the collector 1206) and the energy of the beam after it passes over the grating 1204 (i.e., how much current hits the collector 1206) for a particular emitted frequency. Thus, the absorption of the light at a particular frequency can be indirectly measured by performing energy spectroscopy on the electron beam (i.e., by determining the amount of energy lost by the beam.

The system 1200 is tunable by several methods. For instance, the voltage of the electron beam may be varied. Alternatively, a dynamic (i.e., variable-period) grating 1204 could be incorporated into the system. Finally, an actuator could be coupled to the lid 1230 to vary the position of the reflective surface 1232. Thus, the system 1200 is tunable over a spectrum of terahertz frequencies to facilitate accurate detection of contaminants in a sample.

The system 1200, in which a sample is introduced for analysis via a liquid rather than a gas, may be particularly well-suited for the detection of chemical agents and contaminants, such as pharmaceuticals or narcotics. This is because the molecules in such substances have a tendency to bind to each other, or to proteins or other surfaces. This tendency of the molecules to bind alters the rotational modes of the molecules and restricts the ranges of motion, which in turn modifies the molecules' absorption spectrum.

Figure 13:
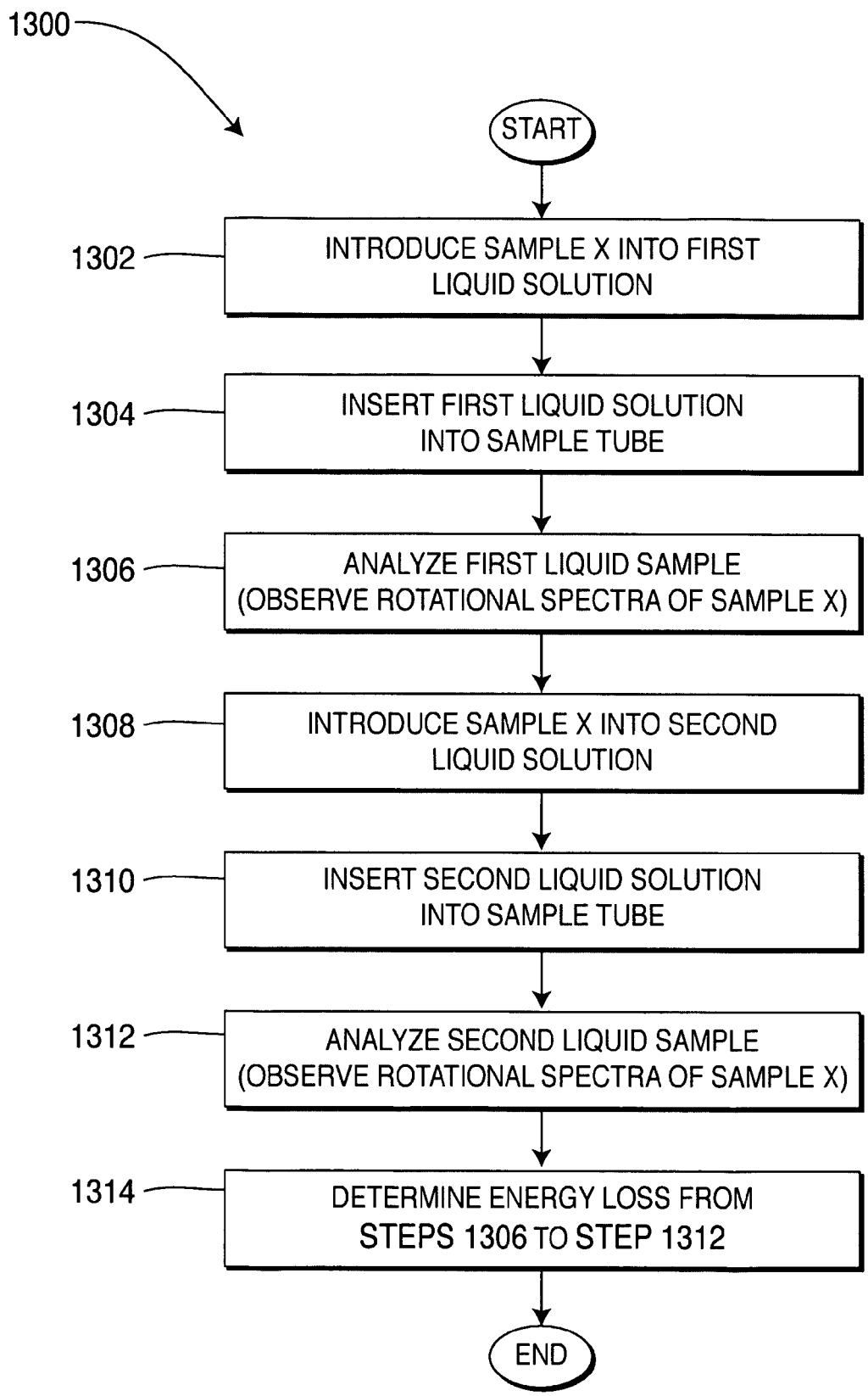
FIG. 13 illustrates a flow diagram of one embodiment of a method for detecting terahertz radiation absorption by a liquid sample.

FIG. 13 illustrates a flow diagram of one embodiment of a method 1300 for detecting terahertz radiation absorption by a liquid sample using the system 1200 illustrated in FIG. 12, in which a sample is introduced into a first liquid solution at step 1302, and this first liquid solution is inserted into the sample tube 1220 for analysis at step 1304. The rotational spectrum of the molecules in the solution are analyzed by the system 1200 by the method described above with reference to FIG. 12, at step 1306. Following analysis of the first liquid solution, a quantity of the same sample material is introduced into a second liquid solution containing at least one binding agent (e.g., a protein) that binds to some of the molecules in the sample, at step 1308. The second solution is inserted into the sample tube 1220 at step 1310 and is analyzed by the system 1200 at step 1312 to determine the altered rotational spectrum of the sample molecules. By comparing the rotational spectra with regard to the first and second liquid samples at step 1314 (i.e., by determining the energy lost in the analyses of the first and second liquid samples), the geometry of the protein-molecule bond can be derived. Thus the degree to which the rotational spectrum of the sample molecules is altered can be used indirectly to identify the chemical composition of the sample.

Figure 14:
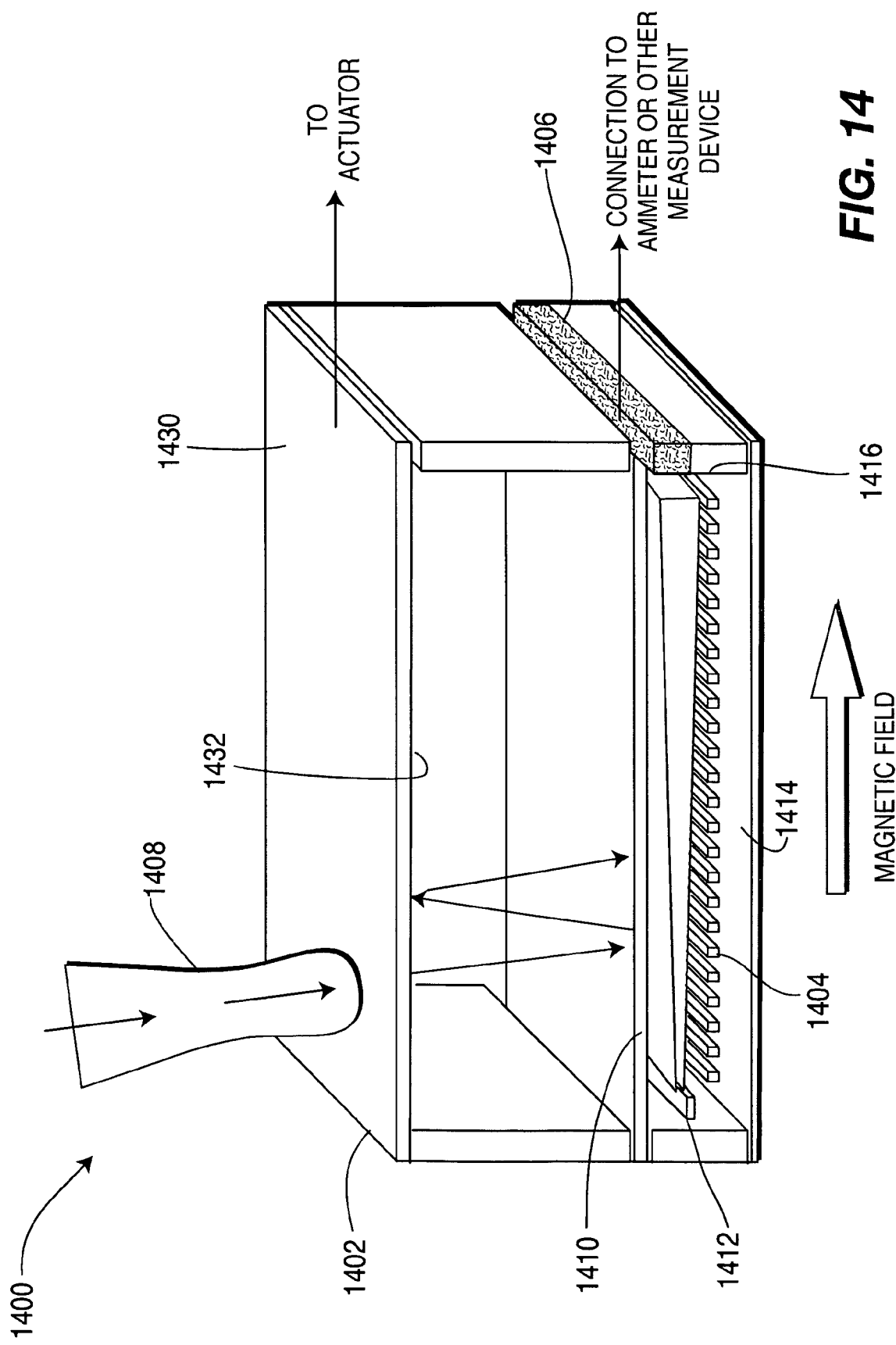
FIG. 14 is a perspective view of an embodiment of a detection system for detecting long wavelength (i.e., low energy) terahertz radiation.

FIG. 14 is a perspective view of an embodiment of a detection system 1400 for detecting long wavelength (i.e., low energy) terahertz radiation. The detector 1400 is structurally similar to the systems 1100 and 1200 illustrated in FIGS. 11 and 12 and comprises a microwave cavity 1402, a grating 1404, a collector 1406, an input pipe 1408, a terahertz transmissive window 1410 and a lid 1430. The grating 1404 is positioned on a lower surface 1414 of the microwave cavity 1402, the interior of which is maintained at a vacuum. The collector 1406 is positioned at one end 1416 of the grating 1404, opposite the point of entry 1412 for an electron beam. The input pipe 1408 is positioned to supply input (e.g., radiation) to the microwave cavity 1402 at an angle substantially normal to the grating 1404. The lid 1430 has a reflective surface 1432 that is positioned to face the transmissive window 1410.

The detection system 1400 works on an "inverse" Smith-Purcell principle. An electron beam is passed closely to the grating 1404. The input pipe 1408 collects radiation from an environment outside of the microwave cavity 1402 and funnels and concentrates the radiation into the microwave cavity 1402. Radiation in the terahertz range will pass through the terahertz transmissive layer 1410 and hit the grating 1404 at an angle substantially normal to the grating 1404. If the captured radiation that strikes the grating 1404 is of a particular wavelength, the radiation will increase the energy of the electrons in the electron beam. The increase in energy will cause the electrons to change their behavior in a spectrometer. The electron beam is then intercepted by the collector 1406, which is connected to a measurement device that observes the increase in energy. In one embodiment, the measurement device is a simple ammeter circuit. The presence of particular wavelengths of radiation in the detector 1400 can therefore be detected by observing an increase in the energy of the electron beam, rather than a decrease as is measured by the systems 1100 and 1200 described above.

In one embodiment, the detection system 1400 is used in conjunction with a solid state source of radiation to detect explosives in an outside environment. The detector 1400 is tunable to detect a chosen Smith-Purcell absorption band, which is accomplished in one embodiment by varying the period of the grating 1404 or the voltage of the electron beam. In another embodiment, the lid 1430 is coupled to an actuator so that the position of the reflective surface 1432 is variable to control the bands of light that are discretized.

Thus the present invention represents a significant advancement in the field of terahertz source technology. A system is provided that enables accurate and efficient detection of chemical and/or biological contaminants. Furthermore, in several embodiments, the invention may be tuned or configured to enhance the accuracy and efficiency of the detection system. The present invention may have further advantages in the fields of imaging, communications and spectroscopy.

A method and apparatus are also provided for generating a spectrum of terahertz radiation. The terahertz source is a continuously tunable electromagnetic wave device that, in several embodiments, exploits the phenomena of Smith-Purcell radiation to produce multiple wavelengths of light.

Smith-Purcell radiation (i.e., far infrared radiation) is produced when an electron beam is passed in a vacuum close to the surface of a periodically modulated conducting surface (e.g., a "grating"). The grating essentially "bunches" the beam and causes the beam to radiate. This produces light having a wavelength that is a function of the periodicity of the grating, the velocity of the electrons, and the angle at which the light is observed relative to the direction of the electron beam. At low voltages, light is typically emitted at an angle normal to the grating.

Figure 15:
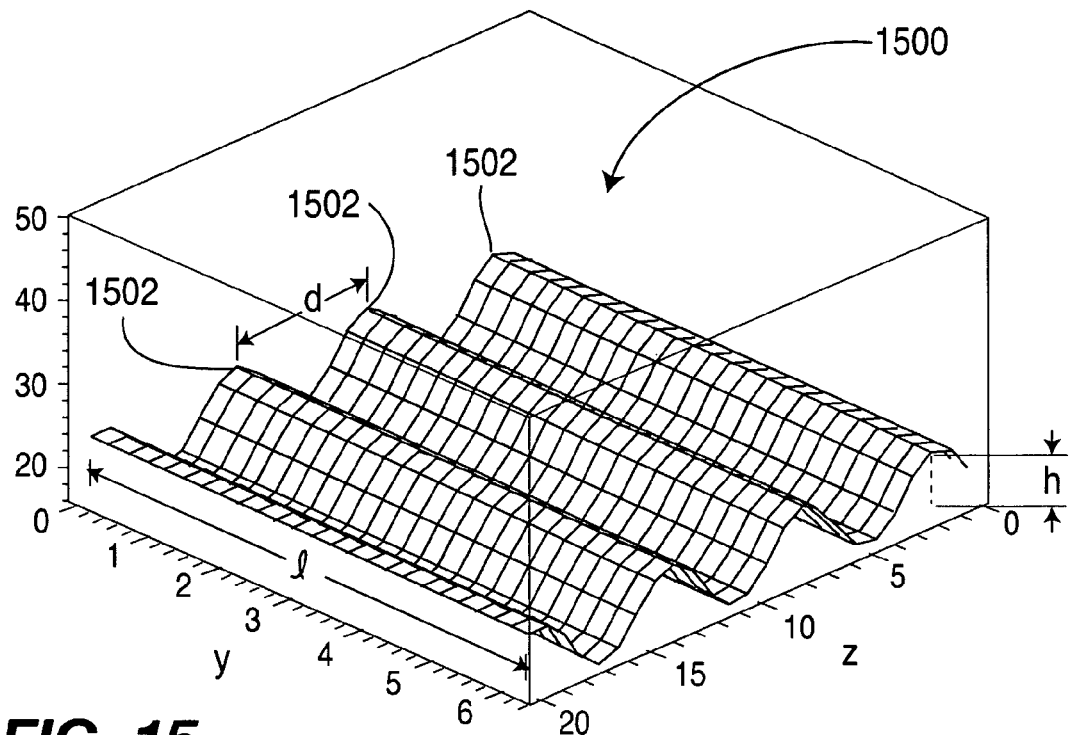
FIG. 15 illustrates a perspective view of a conventional sinusoidal grating that may be used to produce Smith-Purcell radiation.

FIG. 15 illustrates a perspective view of a conventional sinusoidal grating 1500 that may be used to produce Smith-Purcell radiation. The conventional grating 1500 is static—that is, the periodicity is constant, as is evidenced by the peaks 1502 that are each spaced a substantially equal distance d from the next peak 1502. The distance d is substantially constant over the entire length e of adjacent peaks 1502. Furthermore, the peaks 1502 are all of substantially equal height h, and the height h is substantially constant along the entire length e of the peaks 1502. Thus, for example, an electron traveling from $(z, y)=(0, 3)$ to $(z, y)=(20, 3)$ along the z axis will encounter substantially the same conditions as an electron traveling from $(z, y)=(0, 2)$ to $(z, y)=(20, 2)$. Therefore, as long as the velocity of a group of electrons passing over the grating 100 remains constant, light having a single, constant wavelength will be produced.

Figure 16:
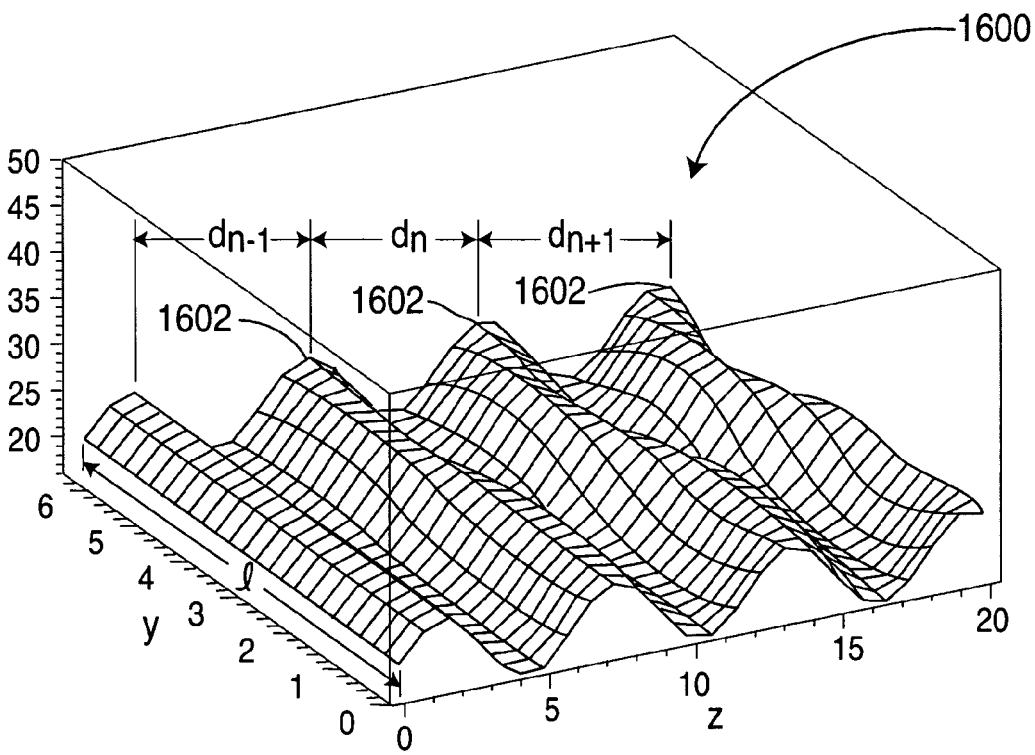
FIG. 16 illustrates a plan view of one embodiment of a grating that may be advantageously adapted for use with the present invention.

FIG. 16 illustrates a plan view of one embodiment of a grating 1600 that may be advantageously adapted for use with the present invention. The periodicity of the grating 1600 is varied in the y direction to form a "deformed" period. That is, a periodic variation is created in the heights of the peaks 1602 along their lengths e and in the distances $d_{n-1}$, $d_n$, $d_{n+1}$, etc. between the peaks 1602. Thus, for example, an electron traveling from (z, y)=(0, 3) to (z, y)=(20, 3) along the z axis will not necessarily encounter the same conditions (i.e., the same period of grating) as an electron traveling from (z, y)=(0, 2) to (z, y)=(20, 2). Therefore, the varying periodicity of the grating 1600 allows a source into which it is integrated to produce light having multiple (or "swept") wavelengths. This is desirable because swept wavelength outputs can be used to perform spectroscopic identification (i.e., by measuring the differential absorption of a target).

Figure 17:
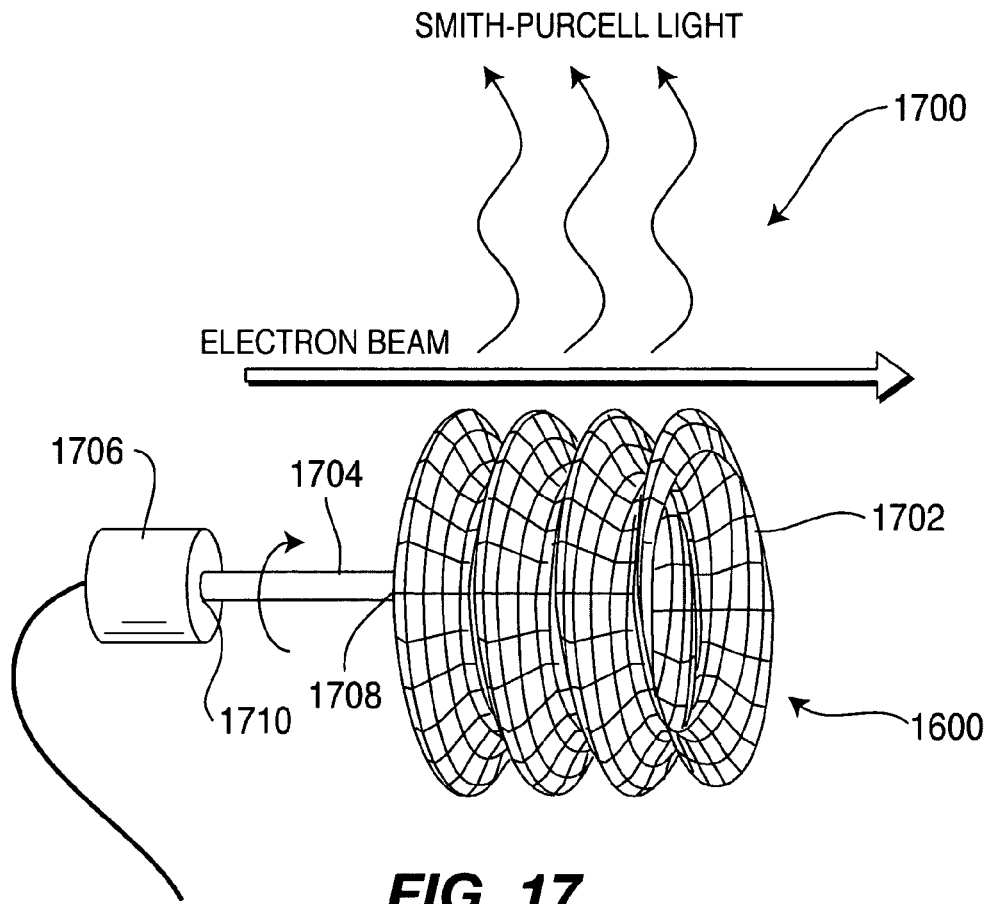
FIG. 17 illustrates a perspective view of one embodiment of a tunable terahertz source device in which the periodically varied grating illustrated in FIG. 16 may be used to advantage.

FIG. 17 illustrates a perspective view of one embodiment of a tunable terahertz source device 1700 in which the periodically varied grating 1600 illustrated in FIG. 16 may be used to advantage. The device 1700 comprises a modulated cylinder 1702, a drive shaft 1704, and a motor 1706. The modulated cylinder comprises the periodically varied grating 1600 illustrated in FIG. 16, mounted to and wrapped around a first end 1708 of the drive shaft 1704. The motor 1706 is coupled to an opposing second end 1710 of the drive shaft. Although the periodically varied grating 1600 is mounted on a cylinder 1702, rotatable surfaces having other shapes may also be used to advantage. In use, the motor 1706 slowly rotates the drive shaft 1704 and cylinder 1702 so that when an electron beam passes closely to the rotating cylinder 1702, the electron beam encounters a grating 1600 whose periodicity varies with the rotation of the cylinder 1702. As the electron beam passes over the periodically varying grating 1600, the Smith-Purcell light that is produced will vary periodically and continuously in time. Thus, the light generated by the device 1700 may be "tuned" to produce various wavelengths of light, while the velocity of the electrons passing over the device 300 remains substantially constant.

Figure 18:
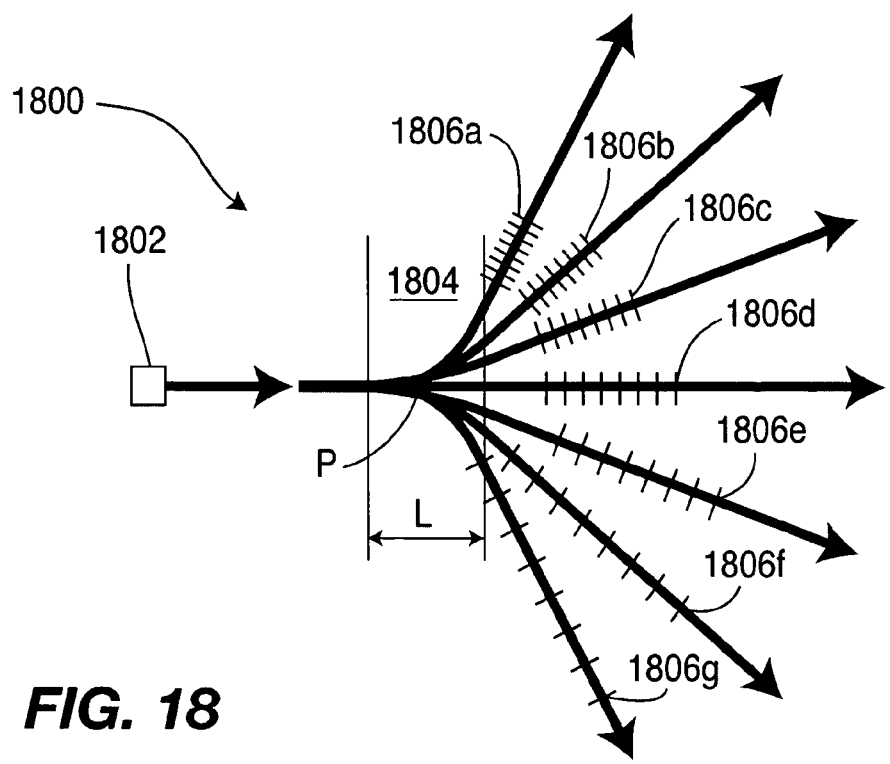
FIG. 18 is a schematic diagram illustrating a second embodiment of a tunable terahertz source device according to the present invention.

FIG. 18 is a schematic diagram illustrating a second embodiment of a tunable terahertz source device 1800 according to the present invention. The device 1800 comprises an electron beam source 1802, a yoke 1804 and at least two sets of substantially uniform-period gratings 1806a-g (hereinafter collectively referred to as "gratings 1806"). Although the embodiment illustrated in FIG. 18 depicts seven sets of gratings 1806, any number of gratings 1806 numbering two or more may be used. In one embodiment, the gratings 1806 radiate outward from a common starting point P at various angles, and the periodicity of each grating 1806 is different (e.g., in the embodiment illustrated in FIG. 18, the "peaks" of grating 1806a are spaced closely together, while the peaks of grating 1806g are spaced further apart). The yoke 1804 is positioned between the electron beam source 1802 and the starting point P of the gratings 1806. The yoke 1804 has at least one aperture (not shown), and the yoke 1804 is movable so that the aperture may be positioned along the axis of any one of the gratings 1806.

Thus, when an electron beam is emitted by the electron beam source 1802, it is received by the yoke 1804, and the beam is deflected along a chosen grating 1806 (depending on how the yoke 1804 is positioned). Thus terahertz source device 1800 is tunable to produce electromagnetic radiation in a broad spectrum. In one embodiment, the device 1800 produces tunable electromagnetic radiation in the ten micron to one millimeter range of the electromagnetic spectrum.

Figure 19:
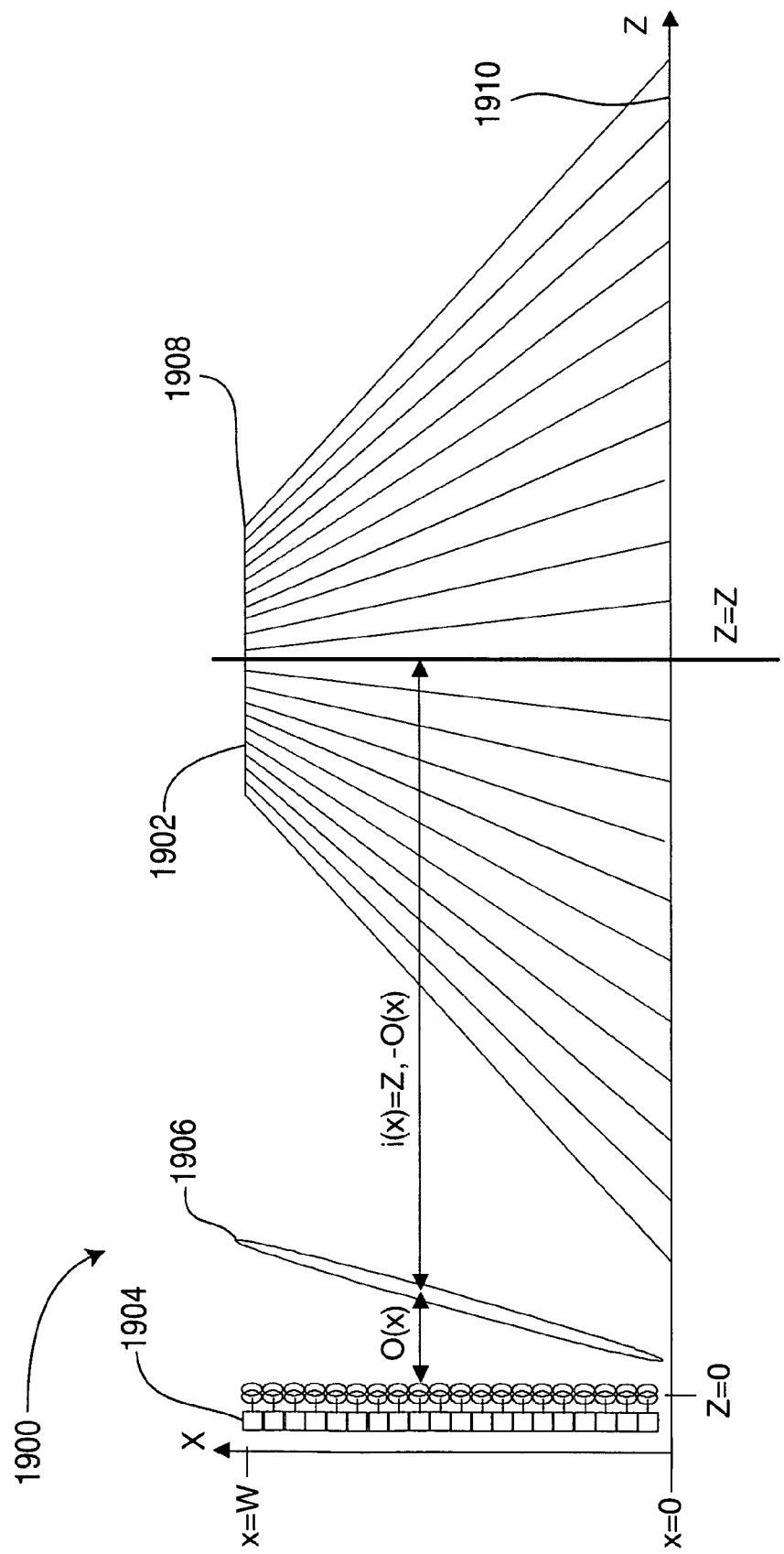
FIG. 19 is a top view of a third embodiment of a terahertz source device according to the present invention.

FIG. 19 is a top view of a third embodiment of a terahertz source device 1900 according to the present invention. The device 1900 comprises a grating 1902 and an array of emitters 1904. The grating 1902 is tapered so that the periodicity of the grating 1902 gradually increases from a first end 1908 of the grating 1902 to a second end 1910 of the grating 1902. The array of emitters 1904 is configured laterally, so that the emitters form a line that is substantially coplanar with the grating 1902. The array of emitters 1904 emits several small electron beams (not shown) that pass closely to the grating 1902 in the form of a sheet. In one embodiment, all beams emitted from the array of emitters 1904 are emitted at the same voltage. When the electron beams simultaneously encounter the grating 1902 having a varying periodicity, each beam radiates at a different frequency so that the device 1900 produces a polychromatic spectrum (i.e., the device 1900 has output at substantially all frequencies simultaneously).

In one embodiment, the device 1900 includes an optional lens 1906 positioned between the array of emitters 1904 and the grating 1902. Each individual electron beam produced by the emitters requires a different focusing parameter depending on the periodicity of the grating that it encounters (e.g., a more rapid focus is needed for a beam traveling over a short period than for a beam traveling over a longer period). The lens 1906 focuses the electron beams produced by the emitters so that the beams are maintained in close proximity to the grating 1902. The lens 1906 has varying optical properties (e.g., focal length) over its surface, and in one embodiment, the lens 1906 is an electrostatic or magnetic lens. Therefore, as the electron beams pass through the lens 1906, each beam encounters a different strength lens. Therefore, the lens 1906 provides the correct focusing to maintain close proximity between the electron beams and the grating 1902 for all periods of the grating 1902, so that maximum output from the device 1900 is obtained.

As illustrated in FIG. 19, the lens 1906 is angled to provide the correct focusing for each electron beam passing therethrough. To achieve proper focusing for all beams emitted by the array of emitters 1904, the waists for all beams must be at the same z location. The focal length f(x) necessary to properly focus a particular beam is dependent upon the distance from the emitter at which the beam originates to the lens 1906, or o(x), and upon the distance from the lens 1906 to the image produced by the beam, or i(x). The proper focal length f(x) may be computed as $$-\frac{M(x)z_f}{(1-M(x))2},$$

wherein M(x) is demagnification and is defined as $$-\frac{i(x)}{o(x)}$$

and $Z_f$ is the z location of the waists of each electron beam. M(x) is always less than zero, so f(x) will always be a positive value.

Figure 20:
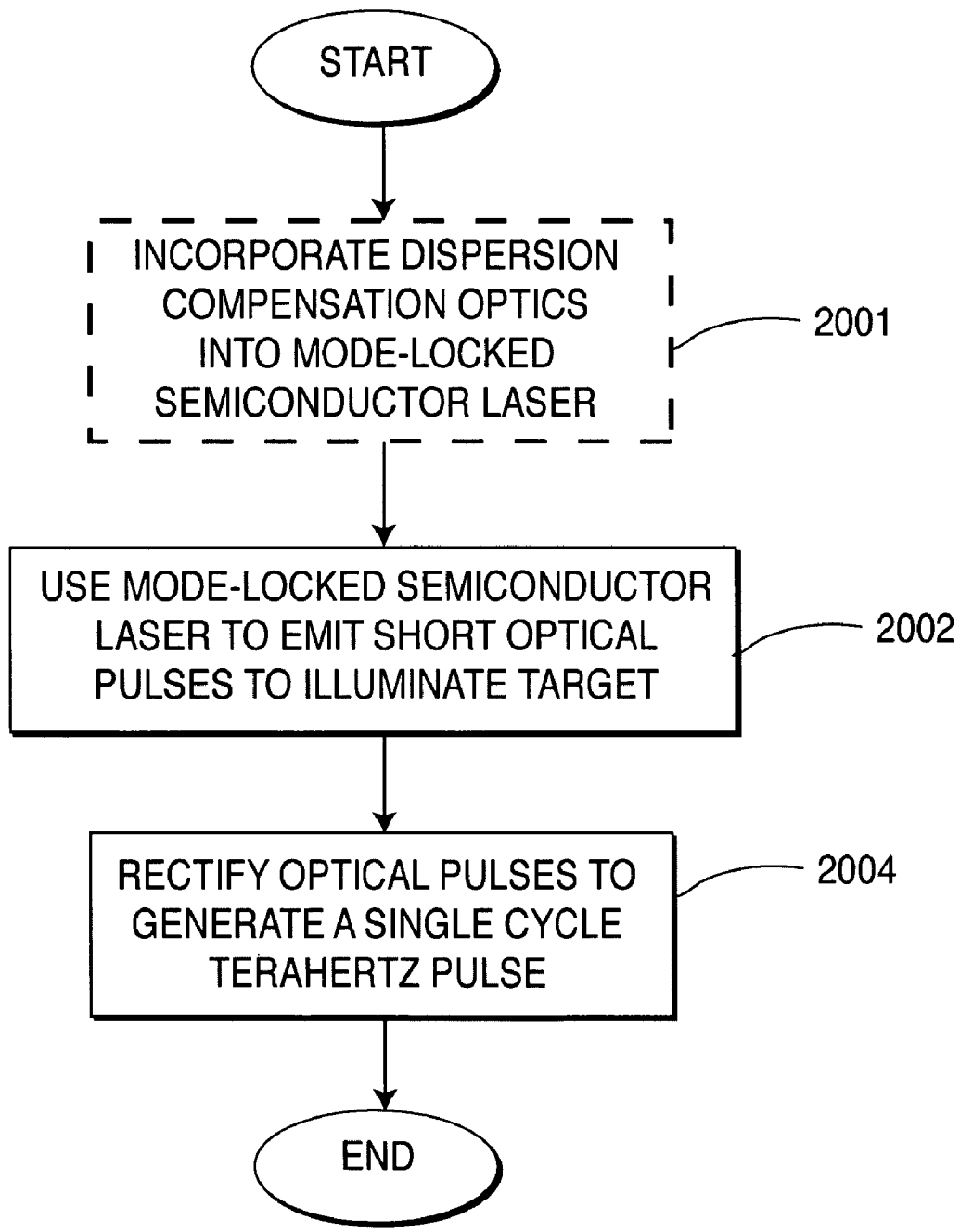
FIG. 20 is a flow diagram illustrating one method for a fourth embodiment of the present invention, in which multiple wavelengths in the far infrared spectrum are produced by a mode-locked semiconductor laser.

FIG. 20 is a flow diagram illustrating one method for a fourth embodiment of the present invention, in which multiple wavelengths in the far infrared spectrum are produced by a mode-locked semiconductor laser. Mode-locked semiconductor lasers are chip-based lasers that produce ultra-short optical pulses. The pulses are sufficiently energetic to produce terahertz emissions when the pulses are incident on a target (e.g., an absorbing semiconductor). One example of a mode-locked semiconductor laser that may be used to advantage with the method illustrated in FIG. 20 is an external cavity semiconductor laser.

As illustrated in FIG. 20, a short optical pulse is emitted from a mode-locked semiconductor laser in step 2002 to illuminate a target. At step 2004, the pulse reaches the target, and the target rectifies the pulse, generating a burst of noise.

The burst of noise includes a broad range of wavelengths. To achieve high frequency terahertz radiation, the shortest possible pulses are emitted from the laser source at step 2002. The highest achievable frequency is given approximately by the inverse of the optical pulse duration. In one embodiment, additional dispersion compensation optics, such as an optional amplifier system, may be incorporated into the laser (at optional step 2001) to shape the gain over the spectrum, thereby producing a more nearly Fourier transform limited pulse.

A mode-locked semiconductor laser is based on solid-state integrated components and may replace lasers having separate components (e.g., mirrors, gain crystal, etc.) by using free-space propagation of light. Therefore, the use of a mode-locked semiconductor laser in the method illustrated in FIG. 20 can produce significant advantages over conventional ultra-short pulse laser-based terahertz systems, which are typically quite large and consume a great deal of power. A mode-locked semiconductor laser and target can be produced in a more compact and portable form than conventional short-pulse laser systems. For example, in one embodiment, the components of the laser are integrated into a single-chip scale device. Thus, mode-locked semi-conductor lasers also typically consume less power than laser systems typically used for the generation of terahertz radiation. Furthermore, because a mode-locked semiconductor laser is a solid state source (as opposed to the vacuum-based electron sources such as those illustrated in FIGS. 16-19), it may offer advantages for a number of other applications including imaging, communications and spectroscopy.

Thus the present invention represents a significant advancement in the field of terahertz source technology. A terahertz radiation source is provided that substantially more compact and efficient than existing terahertz sources. Furthermore, in several embodiments, the invention may be tuned or configured to produce multiple wavelengths of radiation, both individually and simultaneously, thereby facilitating more accurate and efficient detection of contaminants in an analyzed target. The present invention may have further advantages in the fields of imaging, communications and spectroscopy.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

The invention claimed is:

1. A method for sampling high vapor pressure substances, comprising:
   pre-concentrating a sample by compression and condensation;
   removing water in the sample by a condensing gas dryer;
   removing particulates from the sample with an electrostatic precipitator; and
   shuttling the sample through a sintered core at high pressure so that molecules are condensed on the surface of the sintered core.

2. The method of claim 1, wherein the sintered core cools the sample to approximately room temperature.

3. The method of claim 1, further comprising:
   receiving the sample at the sintered core through a heated inlet tube.

4. The method of claim 1, wherein the shuttling is performed by a shuttle having a first piston and a second piston for shuttling the sample through the sintered core, further wherein a condensing heat exchanger is between the first piston and the second piston, the condensing heat exchanger including the sintered core.

5. The method of claim 4, wherein the condensing heat exchanger has a radial configuration.

6. A system for sampling high vapor pressure substances, comprising:
   a shuttle having a first piston and second piston for shuttling a sample through a sintered core at high vapor pressure; and
   a condensing heat exchanger between the first piston and the second piston, the condensing heat exchanger including the sintered core.

7. The system of claim 6, further comprising:
   a heated inlet tube coupled to the sintered core for receiving the sample.

8. The system of claim 6, wherein the condensing heat exchanger has a radial configuration.

9. The system of claim 6, further comprising:
   an electrostatic cleaner for receiving and filtering the sample.

10. The system of claim 6, further comprising:
    a gas dryer coupled to the electrostatic cleaner for extracting water vapor from the sample.

11. The system of claim 6, further comprising:
    a compressor for compressing the sample.

12. The system of claim 6, further comprising:
    a spectrometer for measuring spectra of the sample.

* * * * *